United States Patent
Gombotz et al.

(10) Patent No.: US 9,655,981 B2
(45) Date of Patent: *May 23, 2017

(54) MIXED MICELLES

(71) Applicants: Omeros Corporation, Seattle, WA (US); University of Washington through It's Center for Commercialization, Seattle, WA (US)

(72) Inventors: Wayne R. Gombotz, Kenmore, WA (US); Suzie Pun, Seattle, WA (US); Christopher Mount, Stanford, CA (US); Tae Hee Kim, Suwon (KR); Benjamin W. Dulken, Sammamish, WA (US)

(73) Assignees: Omeros Corporation, Seattle, WA (US); University of Washington through it's center For Commercialization, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/048,098

(22) Filed: Feb. 19, 2016

(65) Prior Publication Data

US 2016/0228580 A1    Aug. 11, 2016

Related U.S. Application Data

(63) Continuation of application No. 13/403,382, filed on Feb. 23, 2012, now Pat. No. 9,295,685.

(60) Provisional application No. 61/466,446, filed on Feb. 24, 2011.

(51) Int. Cl.
| | |
|---|---|
| *A61K 9/00* | (2006.01) |
| *A61K 49/00* | (2006.01) |
| *A61K 31/704* | (2006.01) |
| *A61K 47/34* | (2017.01) |
| *A61K 9/19* | (2006.01) |
| *A61K 49/18* | (2006.01) |
| *A61K 49/04* | (2006.01) |
| *A61K 51/12* | (2006.01) |
| *A61K 9/107* | (2006.01) |

(52) U.S. Cl.
CPC ........ *A61K 49/0082* (2013.01); *A61K 9/0019* (2013.01); *A61K 9/1075* (2013.01); *A61K 9/19* (2013.01); *A61K 31/704* (2013.01); *A61K 47/34* (2013.01); *A61K 49/0034* (2013.01); *A61K 9/107* (2013.01); *A61K 49/0466* (2013.01); *A61K 49/1809* (2013.01); *A61K 51/1227* (2013.01)

(58) Field of Classification Search
None
See application file for complete search history.

(56) References Cited

U.S. PATENT DOCUMENTS

| | | | |
|---|---|---|---|
| 3,740,421 A | 6/1973 | Schmolka et al. | |
| 6,159,445 A * | 12/2000 | Klaveness | B82Y 5/00 424/9.1 |
| 7,297,348 B2 | 11/2007 | Li et al. | |

OTHER PUBLICATIONS

Doi, Y. *Microbial Polyesters*, Chapter 6, pp. 99-106, VCH Publisher, New York (1990).
Herold, D.A., et al., "Oxidation of polyethylene glycols by alcohol dehydrogenase," *Biochem Pharmacol* 38(1):73-76 (1989).
Hirt, T.D., et al,, "Telechelic diols from poly[(R)-3-hydroxybutyric acid] and poly{[(R)-3-hydroxybutyric acid]-co-[(R)-3-hydroxyvaleric acid]}", *Macromol Chem Physic* 197(5):1609-1614 (1996).
Moghimi, S. M., et al., "Long-circulating and target-specific nanoparticles: Theory to practice," *Pharmacol Res* 53(2):283-318 (2001).
Gogolewski, S., et al., "Tissue response and invivo degradation of selected polyhydroxyacids: polylactides (PLA), poly(3-hydroxybutyrate) (PHB), and poly(3-hydroxybutyrate-co-3-hydroxyvalerate) (PHB/VA)," *J Biomed Mater Res* 27(9):1135-1148 (1993).
Li, J., et al., "Synthesis and characterization of new biodegradable amphiphilic poly(ethylene oxide)-b-poly[(R)-3-hydroxy butyratel-b-poly(ethylene oxide) triblock copolymers," *Macromolecules* 36(8):2661-2667 (2003).
Batrakova, E., et al., "Pluronic block copolymers: Evolution of drug delivery concept from inert nanocarriers to biological response modifiers," *J Control Release* 130(2):98-106 (2008).
Werle, M., "Natural and synthetic polymers as inhibitors of drug efflux pumps," *Pharmaceutical Research* 25(3):500-511 (2008).
Danson, S., et al. "Phase I dose escalation and pharmacokinetic study of pluronic polymer-bound doxorubicin (SP1049C) in patients with advanced cancer," *British Journal of Cancer* 90:2085-2091 (2004).
Alakhov, V., et al., "Block copolymer-based formulation of doxorubicin. From cell screen to clinical trials," *Colloids and Surfaces B: Biointelfaces* 16:113-134 (1999).
Yallapu, M. M., et al., "Scope of nanotechnology in ovarian cancer therapeutics," *Journal of Ovarian Research* 3(19):1-10 (2010).
Fortin, J.-P., et al., "Membrane-tethered ligands are effective probes for exploring class B1 G protein-coupled receptor function," *PNAS* 106(19):8049-8054 (2009).
Kim, T.H., et al., "Filamentous, mixed micelles of triblock copolymers enhance tumor localization of indocyanine green in a murine xenograft model," *Mol Pharm* 9(1):135-143 (2012).

(Continued)

*Primary Examiner* — James Rogers
(74) *Attorney, Agent, or Firm* — Marcia S. Kelbon

(57) ABSTRACT

This disclosure is directed to mixed micelle compositions for administration of e.g., therapeutic agents or imaging agents to a subject.

11 Claims, 11 Drawing Sheets

(56) References Cited

OTHER PUBLICATIONS

Figure 1:
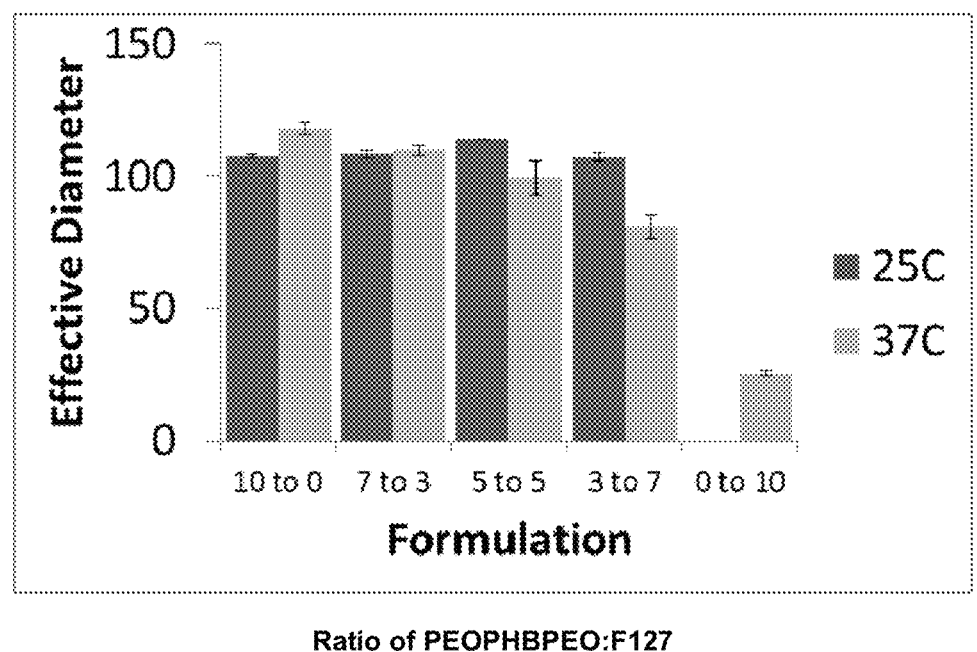

Kim, T.H., et al., "The delivery of doxorubicin to 3-D multicellular spheroids and tumors in a murine xenocrafts model using tumor-penetrating triblock polymeric micelles," *Biomaterials* 31(20):7386-7397 (2010).
Kim, T.H., et al., Evaluation of temperature-sensitive, indocyanine green-encapsulating micelles for noninvasive near-infrared tumor imaging, *Pharm Res* 27(9):1900-1913 (2010).
Mei, L., et al., "A novel docetaxel-loaded poly (ε-caprolactone)/pluronic F68 nanoparticle overcoming multidrug resistance for breast cancer treatment," *Nanoscale Res Lett* 4:1530-1539 (2009).
Kim, T.H., "PEO-PHB-PEO Micelles for Tumor Imaging and Therapy," Slide Show, Aug. 11, 2010.
Li, X., et al., "Novel mixed polymeric micelles for enhancing delivery of anticancer drug and overcoming multidrug resistance in tumor cell lines simultaneously," *Pharm Res* 27:1498-1511 (2010).
Gondi, C. S., et al., "Concepts in in vivo siRNA delivery for cancer therapy," *J Cell Physiol* 220(2):285-291 (2009).
Xiong, X.B., et al., "The therapeutic response to multifunctional polymeric nano-conjugates in the targeted cellular and subcellular delivery of doxorubicin," *Biomaterials* 31(4):757-768 (2009).
Kim, J.O., et al., "Polymer micelles with cross-linked polyanion core for delivery of a cationic drug doxorubicin," *J Contro Release* 138(3):197-204 (2009).
Ganz, W.I., et al., "Review of tests for monitoring doxorubicin-induced cardiomyopathy," *Oncology* 53(6):461-470 (1996).
Iyer, A.K., et al., "Exploiting the enhanced permeability and retention effect for tumor targeting," *Drug Discov Today* 11(17-18):812-818 (2006).
Rapoport, N., et al., "Intracellular uptake and trafficking of Pluronic micelles in drug-sensitive and MDR cells: effect on the intracellular drug localization," *J Pharm Sci* 91(1):157-170 (2002).
Rapoport, N., et al., "Multifunctional nanoparticles for combining ultrasonic tumor imaging and targeted chemotherapy," *J Natl Cancer Inst* 99(14):1095-1106 (2007).
Gabizon, A., et al., "Pharmacokinetics of pegylated liposomal Doxorubicin: review of animal and human studies," *Clin Pharmacokinet* 42(5):419-436 (2003).
O'Brien, M.E., et al., "Reduced cardiotoxicity and comparable efficacy in a phase III trial of pegylated liposomal doxorubicin HCI (CAELYX/Doxil) versus conventional doxorubicin for first-line treatment of metastatic breast cancer," *Ann Oncol* 15(3):440-449 (2004).
Mikhail, A.S., et al., "Block copolymer micelles for delivery of cancer therapy: transport at the shole body, tissue and cellular levels," *J Control Release* 138(3):214-223 (2009).
Liu, H., et al., "Drug release characteristics of unimolecular polymeric micelles," *J Control Release* 68(2):167-174 (2000).
Moghimi, S.M., et al., "Non-phagocytic uptake of intravenously injected microspheres in rat spleen: influence of particle size and hydrophilic coating," *Biochem Biophys Res Commun* 177(2):861-866 (1991).
Yuan, F., et al., "Vascular permeability in a human tumor xenografts: molecular size dependence and cutoff size," *Cancer Res* 55(17):3752-3756 (1995).
Stolnik, S., et al., "Circulating microparticulate drug carriers," *Advanced Drug Delivery Reviews* 16(2-3):195-214 (1995).
Lavasanifar, A., et al., "Poly(ethylene oxide)-block-poly(L-amino acid) micelles for drug delivery," *Adv Drug Deliv Rev* 54(2):169-190 (2002).
Gaucher, G., et al., "Block copolymer micelles: preparation, characterization and application in drug delivery," *J Control Release* 109(1-3):169-188 (2005).
Li, X., et al., "Dynamic and static light scattering studies on self-aggregation behavior of biodegradable amphiphilic poly(ethylene oxide)-poly[(R)-3-hydroxybutyrate]-poly(ethylene oxide) triblock copolymers in aqueous solution," *J Phys Chem B* 110(12):5920-5926 (2006).

Reusch, R.N., et al., "Transport of poly-beta-hydroxybutyrate in human plasma," *Biochim Biophys Acta* 1123(1):33-40 (1992).
Freier, T., et al., "In vitro and in vivo degradation studies for development of a biodegradable patch based on poly(3-hydroxybutyrate),"*Biomateriais* 23(13):2649-2657 (2002).
Missirlis, D., et al., "Doxorubicin encapsulation and diffusional release from stable, polymeric, hydrogel nanoparticles," *Eur J Pharm Sci* 29(2):120-129 (2006).
Goodman, T.T., et al., "Increased nanoparticle penetration in collagenase-treated multicellular spheroids," *Int J Nanomedicine* 2(2):265-274 (2007).
Wong, H.L., et al., "A mechanistic study of enhanced doxorubiein uptake and retention in multidrug resistant breast cancer cells using a polymer-lipid hybrid nanoparticie system," *J Pharmacol Exp Ther* 317(3):1372-1381 (2006).
Minchinton, A.I., et al., "Drug penetration in solid tumours," *Nat Rev Cancer* 6(8):583-592 (2006).
Sutherland, R.M., "Cell and environment interactions in tumor microregions: the multicell spheroid model," *Science* 240(4849):177-184 (1988).
Hall, M.D., et al., "Comparative efficacy of novel platinum(IV) compounds with established chemotherapeutic drugs in solid tumour models," *Biochem Pharmacol* 67(1):17-30 (2004).
Bryce, N.S., et al., "Accumulation of an anthraquinone and its platinum complexes in cancer cell spheroids: the effect of charge on drug distribution in solid tumour models," *Chem Commun (Camb)* 19:2673-2675 (2009).
Goodman, T.T., et al., "3-D tissue culture systems for the evaluation and optimization of nanopartiele-based drug carriers," *Bioconjug Chem* 19(10):1951-1959 (2008).
Fadok, V.A., et al., "Exposure of phosphatidylserine on the surface of apoptotic lymphocytes triggersspecific recognition and removal by macrophages," *J Immunol* 148(7):2207-2216 (1992).
Frenkel, V., "Ultrasound mediated delivery of drugs and genes to solid tumors," *Adv Drug Deliv Rev* 60(10):1193-1208 (2008).
Wang, Y., et al., "Delivery of viral vectors to tumor cells: extracellular transport, systemic distribution, and strategies for improvement," *Ann Biomed Eng* 34(1):114-127 (2006).
Galmarini, C.M., et al., "Multidrug resistance in cancer therapy: role of the microenvironment," *Curr Opin Investig Drugs* 4(12):1416-1421 (2003).
Tannock, I.F., et al., "Acid pH in tumors and its potential for therapeutic exploitation," *Cancer Res* 49(16):4373-4384 (1989).
Jain, R.K., "Vascular and interstitial barriers to delivery of therapeutic agents in tumors," *Cancer Metastasis Rev* 9(3):253-266 (1990).
Harris, A.L., "Hypoxia—a key regulatory factor in tumour growth," *Nat Rev Cancer* 2(1):38-47 (2002).
Fracasso, G., et al., "Effect of therapeutic macromolecules in spheroids," *Crit Rev Oncol Hematol* 36(2-3):159-178 (2000).
Kerr, D.J., et al., "Cytotoxic drug penetration studies in multicellular tumour spheroids," *Xenobiotica* 18(6):641-648 (1988).
Davies, C.D., et al., "Comparison of extracellular matrix in human osteosarcomas and melanomas growing as xenografts, multicellular spheroids, and monolayer cultures," *Anticancer Res* 17(6D):4317-4326 (1997).
Durand, R.E., "Slow penetration of anthracyclines into spheroids and tumors: a therapeutic advantage?" *Cancer Chemother Pharmacol* 26(3):198-204 (1990).
Primeau, A.J., et al., "The distribution of the anticancer drug Doxorubicin in relation to blood vessels in solid tumors," *Clin Cancer Res* 11(24 Pt 1):8782-8788 (2005).
Lankelma, J., et al., "Doxorubicin gradients in human breast cancer," *Clin Cancer Res* 5(7):1703-1707 (1999).
Tang, N., et al., "Improving penetration in tumors with nanoassemblies of phospholipids and doxorubicin," *J Natl Cancer Inst* 99(13):1004-1015 (2007).
Ng, C.P., et al., "A perfusable 3D cell-matrix tissue culture chamber for in situ evaluation of nanoparticle vehicle penetration and transport," *Biotechnol Bioeng* 99(6):1490-1501 (2008).
Pluen, A., et al., "Role of tumor-host interactions in interstitial diffusion of macromolecules: cranial vs. subcutaneous tumors," *Proc Natl Acad Sci USA* 98(8):4628-4633 (2001).

(56) References Cited

OTHER PUBLICATIONS

Hwang, S.J., et al., "Cationic polymers for gene delivery: designs for overcoming barriers to systemic administration," *Curr Opin Mol Ther* 3(2):183-191 (2001).

Han, M., et al., "Enhanced percolation and gene expression in tumor hypoxia by PEGylated polyplex micelles," *Mol Ther* 17(8):1404-1410 (2009).

Tsukioka, Y., et al., "Pharmaceutical and biomedical differences between micellar doxorubicin (NK911) and liposomal doxorubicin (Doxil)," *Jpn J Cancer Res* 93(10):1145-1153 (2002).

Hoang, B., et al., "Noninvasive monitoring of the fate of 111In-labled block copolymer micelles by high resolution and high sensitivity microSPECT/CT imaging," *Mol Pharm* 6(2):581-592 (2009).

Chen, H., et al., "Release of hydrophobic molecules from polymer micelles into cell membranes revealed by Forster resonance energy transfer imaging," *Proc Natl Acad Sci USA* 105(18):6596-6601 (2008).

Venne, A., et al., "Hypersensitizing effect of pluronic L61 on cytotoxic activity, transport, and subcellular distribution of doxorubicin in multiple drug-resistant cells," *Cancer Res* 56(16):3626-3629 (1996).

Allen, C., et al., "Cellular internalization of PCL(20)-b-PEO(44) block copolymer micelles," *Biochim Biophys Acta* 1421(1):32-38 (1999).

Savic, R., et al., "Micellar nanocontainers distrubte to defined cytoplasmic organelles," *Science* 300(5619):615-618 (2003).

Lammers, T., et al., "Effect of intratumoral injection on the diodistribution and the therapeutic potential of HPMA copolymer-based drug delivery systems," *Neoplasia* 8(10):788-795 (2006).

Kim, D., et al., "In vivo evaluation of doxorubicin-loaded polymeric micelles targeting folate receptors and early endosomal pH in drug-resistance ovarian cancer," *Mol Pharm* 6(5): 1353-1362 (2009).

Chytil, P., et al., "New substituents for solid tumour targeting," *J Control Release* 127(2):121-130 (2008).

Kataoka, K., et al., "Block copolymer micelles for drug delivery: design, characterization and biological significance," *Adv Drug Deliv Rev* 47(1):113-131 (2001).

Hu, F.Q., et al., "Shell cross-linked stearic acid grafted chitosan oligosaccharide self-aggregated micelles for controlled release of paclitaxel," *Colloids Surf B Biointerfaces* 50(2):97-103 (2006).

Batrakova, E.V., et al., "Distribution kinetics of a micelle-firming block copolymer Pluronic P85," *J Control Release* 100(3):389-397 (2004).

Kim, T.H., et al., "Mannosylated chitosan nanoparticle-based cytokine gene therapy suppressed cancer growth in BALB/c mice bearing CT-26 carcinoma cells," *Mol Cancer Ther* 5(7): 1723-1732 (2006).

Rodriguez, V.B., et al., "Encapsulation and stabilization of indocyanine green within poly(styrene-alt-maleic anhydride) block-poly(styrene) micelles for near-infrared imaging," *J Biomed Optics* 13(1): 014025-1-014025-10 (2008).

Holland, P.,et al., "Mixed surfactant systems-an overview," *ACS Symposium Series 501*, Chapter 1, pp. 2-30 (1992).

Cherrick, G.R., et al., "Indocyanine green: observations on its physical properties, plasma decay, and hepatic extraction," *J Clin Invest* 39:592-600 (1960).

Kirchherr, A.K., et al., "Stabilization of indocyanine green by encapsulation within micellar systems," *Mol Pharm* 6(2):480-491 (2009).

Altinoglu, E.I., et al., "Near infrared imaging with nanoparticles," *Wiley Interdiscip Rev Nanomed Nanobiotechnol* 2(5):461-477 (2010).

Saxena, V., et al., "Enhanced photo-stability, thermal-stability and aqueous-stability of indocyanine green in polymeric nanoparticulate systems," *J Photochem Photobiol B* 74(1):29-38 (2004).

Yin, H., et al., "Physiochemical aspects of doxoruhicin-loaded pH-sensitive micelle formulations from mixture of poly(L-histidine)-b-poly(ethylene glycol)/poly(L-lactide)-b-poly(ethylerie glycol)," *Eur J Pharm Biopharm* 71(2):223-230 (2009).

* cited by examiner

MIXED MICELLES

CROSS REFERENCE TO RELATED APPLICATIONS

This application is a continuation of pending U.S. patent application Ser. No. 13/403,382, filed Feb. 23, 2012, which claims the benefit of the filing date of U.S. Provisional Patent Application Ser. No. 61/446,446 filed Feb. 24, 2011.

I. FIELD OF THE INVENTION

This disclosure is directed to mixed micelle compositions for administration of e.g., therapeutic agents or imaging agents to a subject.

II. BACKGROUND OF THE INVENTION

A wide variety of agents are administered to subjects, e.g., to treat diseases or disorders or to provide assistance in diagnosing a disease or disorder. Some potential agents are not appropriate for administration to a subject, e.g., because the agent is very hydrophobic and not able to be formulated in a manner consistent with efficient administration, or because the agent is unstable in a physiologic environment. Other agents can be administered to a subject, but their efficacy would be improved by selective targeting to a particular site in the body. The present invention solves these and other problems.

III. SUMMARY OF THE INVENTION

In one aspect the present invention provides a mixed micelle that includes a poly(ethylene oxide)-poly[(R)-3-hydroxybutyrate]-poly(ethylene oxide) (PEO-PHB-PEO) molecule and a poly(ethylene oxide)-poly(propylene oxide-poly(ethylene oxide) (PEO-PPO-PEO) molecule. The mixed micelles can include or encapsulate a therapeutic agent or an imaging agent and are useful for a variety of purposes.

In one embodiment, the mixed micelle includes one of the following PEO-PHB-PEO molecules: PEO-PHB1.4k-PEO, PEO-PHB2.5k-PEO, and PEO-PHB3.2k-PEO, in which the average molecular weight of the PHB used in the molecule is 1,400, 2,500 and 3,200, respectively. In one embodiment, the mixed micelles include the following PEO-PPO-PEO molecule: PF-127. In another embodiment, the ratio of PEO-PHB-PEO to PEO-PPO-PEO used to make the mixed micelle is, e.g., about 10:1, about 7:3, about 5:5, or about 3:7. In a further embodiment, the ratio of PEO-PHB-PEO to PEO-PPO-PEO used to make the mixed micelle is about 7:3.

In one embodiment, the mixed micelle includes an agent that is a therapeutic agent. In a further embodiment, the therapeutic agent is a chemotherapeutic agent. The chemotherapeutic agent encapsulated in the PEO-PHB-PEO/PEO-PPO-PEO mixed micelles can be, e.g., doxorubicin, adriamycin, paclitaxel, docetaxel, actinomycin D, daunorubicin, valrubicin, idarubicin, epirubicin, bleomycin, plicamycin, camptothecin and derivatives, bleomycin, etoposide, teniposide, mitomycin, vinca alkaloids, such as vinblastine and vincristine, or platinum-based compounds such as cisplatin, gemcitabine. Mixed micelles can also encapsulate other therapeutic agents, e.g., analgesics, anesthetics, anti-arthritic drugs, disease modifying anti-rheumatic drugs (DMARDS), anti-asthma drugs, anticoagulants, anticonvulsants, antidepressants, antidiabetics, antipsychotics, antihypertensives, antibiotics, antihistamines, decongestants, anti-inflammatories, muscle relaxants, anti-parasitic drugs, antiviral drugs, anti-restenotic agents, anti-spasm agents, chondroprotective agents, anti-adhesion agents, anti-tumor cell invasion agents, vasorelaxants, vasoconstrictors, immunosupressants, peptides, proteins, cytokines, growth factors, angiogenesis factors, soluble receptors, antibodies and fragments thereof, human recombinant proteins, small molecules, antigens (e.g., vaccines), antisense RNA, and siRNA molecules. In a further embodiment, the mixed micelles of the invention encapsulate doxorubicin.

In one embodiment, the mixed micelle encapsulates an agent that is an imaging agent. Imaging agents that can be encapsulated in the mixed micelles include, e.g., indocyanine green (ICG), paramagnetic metals such as gadolinium or manganese, iron oxide nanoparticles, quantum dots, and heavy elements such as iodine or barium.

In one embodiment, the size of the mixed micelle is between 10-120 nm. In another embodiment, the size of the mixed micelle is between 50-120 nm. In a further embodiment, the size of the micelle is about 110 nm. In another embodiment, the mixed micelle is a filamentous micelle.

In one embodiment, the following ratios of PEO-PHB-PEO to PEO-PPO-PEO are found in the mixed micelles: 7:3, 5:5, 3:7, 10:0, 9:1, 8:2, 6:4, 4:6, 2:8, and 1:9. In a further embodiment, the following ratios of PEO-PHB-PEO to PEO-PPO-PEO are found in the mixed micelles: about 7:3, about 5:5, about 3:7, about 10:0, about 9:1, about 8:2, about 6:4, about 4:6, about 2:8, and about 1:9.

In one embodiment the PEO-PHB-PEO/PEO-PPO-PEO mixed micelles are suspended in a pharmaceutical composition.

In one aspect, the present invention provides a method of delivering an imaging agent to a subject, by administering a PEO-PHB-PEO/PEO-PPO-PEO mixed micelle that encapsulates the imaging agent to the subject. Imaging agents that can be used in this method include, e.g., indocyanine green (ICG), paramagnetic metals such as gadolinium or manganese, iron oxide nanoparticles, quantum dots, and heavy elements such as iodine or barium. In one embodiment, the imaging agent is indocyanine green (ICG). In one embodiment, the subject is a human subject.

In one embodiment, the imaging agent is more stable in the subject when administered in the mixed micelle, than when administered in an aqueous solution. In another embodiment, the subject has a tumor and the mixed micelle comprising the imaging agent is preferentially taken up by the tumor. In a further embodiment, the method includes a step of visualizing the imaging agent in the subject.

In one aspect, the present invention provides a method of delivering a chemotherapeutic agent to a subject, by administering a PEO-PHB-PEO/PEO-PPO-PEO mixed micelle that encapsulates the chemotherapeutic agent to the subject. Chemotherapeutic agents can be e.g., an antibody, a protein, a peptide, an anti-sense molecule, a small inhibitory RNA (siRNA) molecule, or a small molecule. Exemplary chemotherapeutic agents for use in this delivery method are doxorubicin, adriamycin, paclitaxel, docetaxel, actinomycin D, daunorubicin, valrubicin, idarubicin, epirubicin, bleomycin, plicamycin, camptothecin and derivatives, bleomycin, etoposide, teniposide, mitomycin, vinca alkaloids, such as vinblastine and vincristine, and platinum-based compounds such as cisplatin, gemcitabine. In one embodiment, the chemotherapeutic agent is doxorubicin. In one embodiment, the chemotherapeutic agent loaded mixed micelles are administered to a human subject.

In one embodiment, the chemotherapeutic agent is more stable in the subject when administered in the mixed micelle, than when administered in an aqueous solution. In another embodiment, the subject has a tumor and the mixed micelle comprising the chemotherapeutic agent is preferentially taken up by the tumor. In a further aspect the tumor includes multi-drug resistant cancer cells.

In one aspect invention provides a method of treating cancer in a subject by administering a chemotherapeutic agent to the subject, by way of a mixed micelle comprising a poly(ethylene oxide)-poly[(R)-3-hydroxybutyrate]-poly (ethylene oxide) (PEO-PHB-PEO) molecule and a poly (ethylene oxide)-poly(propylene oxide-poly(ethylene oxide) (PEO-PPO-PEO) molecule that encapsulates the chemotherapeutic agent. In one embodiment, the mixed micelle is a filamentous micelle. In another embodiment, the subject is a human subject.

In one embodiment, the mixed micelle comprising the chemotherapeutic agent is preferentially taken up by cancer cells in the subject. In a further embodiment, the subject has a solid tumor and the mixed micelle comprising the chemotherapeutic agent is preferentially taken up by the solid tumor.

For this cancer treatment method, chemotherapeutic agents can be e.g., an antibody, a protein, a peptide, an anti-sense molecule, a small inhibitory RNA (siRNA) molecule, or a small molecule. Exemplary chemotherapeutic agents for use in this delivery method are doxorubicin, adriamycin, paclitaxel, docetaxel, actinomycin D, daunorubicin, valrubicin, idarubicin, epirubicin, bleomycin, plicamycin, camptothecin and derivatives, bleomycin, etoposide, teniposide, mitomycin, vinca alkaloids, such as vinblastine and vincristine, and platinum-based compounds such as cisplatin, gemcitabine. In one embodiment, the chemotherapeutic agent is doxorubicin. In a further embodiment, the cancer is a multi-drug resistant (MDR) cancer.

In one aspect the present invention provides a method of inhibiting growth of a cancer cell, by contacting the cancer cell with a chemotherapeutic agent that is encapsulated in a mixed micelle comprising a poly(ethylene oxide)-poly[(R)-3-hydroxybutyrate]-poly(ethylene oxide) (PEO-PHB-PEO) molecule and a poly(ethylene oxide)-poly(propylene oxide-poly(ethylene oxide) (PEO-PPO-PEO) molecule. In one embodiment, the mixed micelle is a filamentous micelle.

For this method of inhibiting cancer cell growth, chemotherapeutic agents can be e.g., an antibody, a protein, a peptide, an anti-sense molecule, a small inhibitory RNA (siRNA) molecule, or a small molecule. Exemplary chemotherapeutic agents for use in this delivery method are doxorubicin, adriamycin, paclitaxel, docetaxel, actinomycin D, daunorubicin, valrubicin, idarubicin, epirubicin, bleomycin, plicamycin, camptothecin and derivatives, bleomycin, etoposide, teniposide, mitomycin, vinca alkaloids, such as vinblastine and vincristine, and platinum-based compounds such as cisplatin, gemcitabine. In one embodiment, the chemotherapeutic agent is doxorubicin. In a further embodiment, the cancer is a multi-drug resistant (MDR) cancer.

In one aspect the present invention provides a method of making a mixed micelle comprising a poly(ethylene oxide)-poly[(R)-3-hydroxybutyrate]-poly(ethylene oxide) (PEO-PHB-PEO) molecule and a poly(ethylene oxide)-poly(propylene oxide-poly(ethylene oxide) (PEO-PPO-PEO) molecule, by combining the PEO-PHB-PEO molecules and the PEO-PPO-PEO molecules and allowing the mixed micelles to form. The PEO-PHB-PEO molecules and the PEO-PPO-PEO molecules are present a concentration higher than their critical micellar concentration (CMC).

The size of the mixed micelles can be controlled using this method. In one embodiment, the size of the mixed micelle is between 10-120 nm. In another embodiment, the size of the mixed micelle is between 50-120 nm. In a further embodiment, the size of the micelle is about 110 nm. In another embodiment, the mixed micelle is a filamentous micelle.

The ratio of PEO-PHB-PEO to PEO-PPO-PEO can be varied. In one embodiment, the following ratios of PEO-PHB-PEO to PEO-PPO-PEO are found in the mixed micelles: 7:3, 5:5, 3:7, 10:0, 9:1, 8:2, 6:4, 4:6, 2:8, and 1:9. In a further embodiment, the following ratios of PEO-PHB-PEO to PEO-PPO-PEO are found in the mixed micelles: about 7:3, about 5:5, about 3:7, about 10:0, about 9:1, about 8:2, about 6:4, about 4:6, about 2:8, and about 1:9.

In another embodiment, the mixed micelles are suspended in a pharmaceutical carrier.

In one embodiment, an imaging agent is encapsulated in the mixed micelle. Exemplary imaging agents include, e.g., indocyanine green (ICG), paramagnetic metals such as gadolinium or manganese, iron oxide nanoparticles, quantum dots, and heavy elements such as iodine or barium. In one embodiment, mixed micelles that encapsulate ICG are made.

In one embodiment, a chemotherapeutic agent is encapsulated in the mixed micelle. For this method of making a mixed micelle, chemotherapeutic agents can be e.g., an antibody, a protein, a peptide, an anti-sense molecule, a small inhibitory RNA (siRNA) molecule, or a small molecule. Exemplary chemotherapeutic agents for use in this delivery method are doxorubicin, adriamycin, paclitaxel, docetaxel, actinomycin D, daunorubicin, valrubicin, idarubicin, epirubicin, bleomycin, plicamycin, camptothecin and derivatives, bleomycin, etoposide, teniposide, mitomycin, vinca alkaloids, such as vinblastine and vincristine, and platinum-based compounds such as cisplatin, gemcitabine. In one embodiment, the chemotherapeutic agent is doxorubicin.

IV. BRIEF DESCRIPTION OF THE DRAWINGS

The present invention will now be described in greater detail, by way of example, with reference to the accompanying drawings in which:

FIG. 1 provides particle size analysis of ICG-loaded PEO-PHB-PEO:PEO-PPO-PEO mixed micelles suspended in phosphate buffered saline (PBS).

Figure 2:
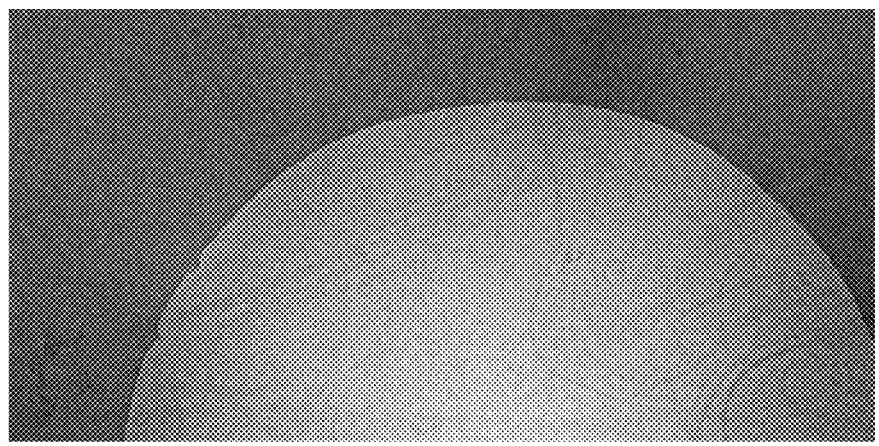

FIG. 2 shows a cryo-transmission micrograph of ICG-loaded PEO-PHB-PEO:PEO-PPO-PEO mixed micelles (7:3 ratio) that assemble into filamentous structures.

Figure 3:
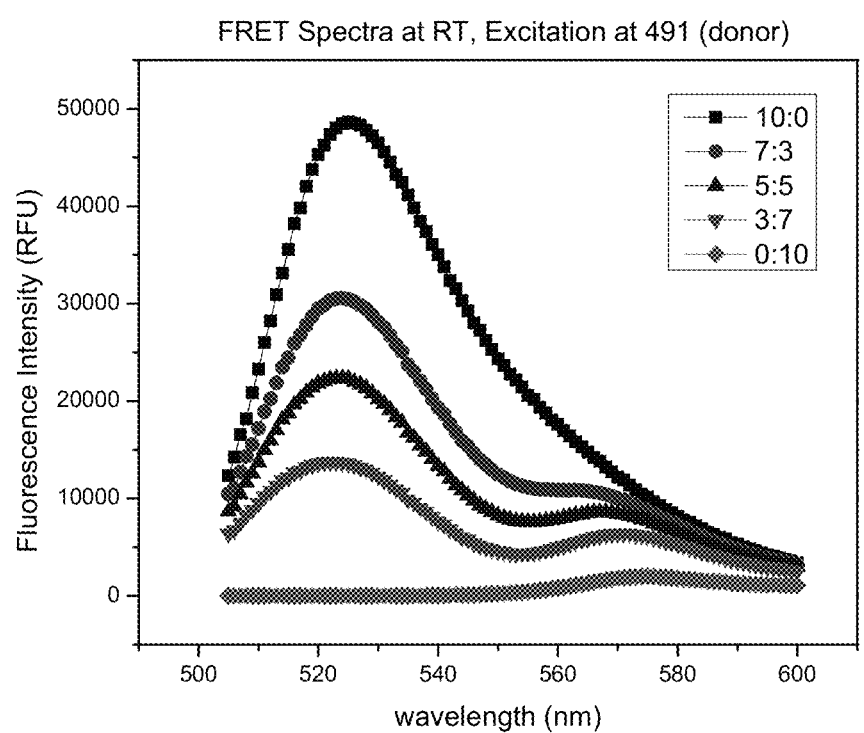

FIG. 3 provides fluorescence resonance energy transfer (FRET) behavior in PEO-PHB-PEO:PEO-PPO-PEO mixed micelle formulations.

Figure 4A:
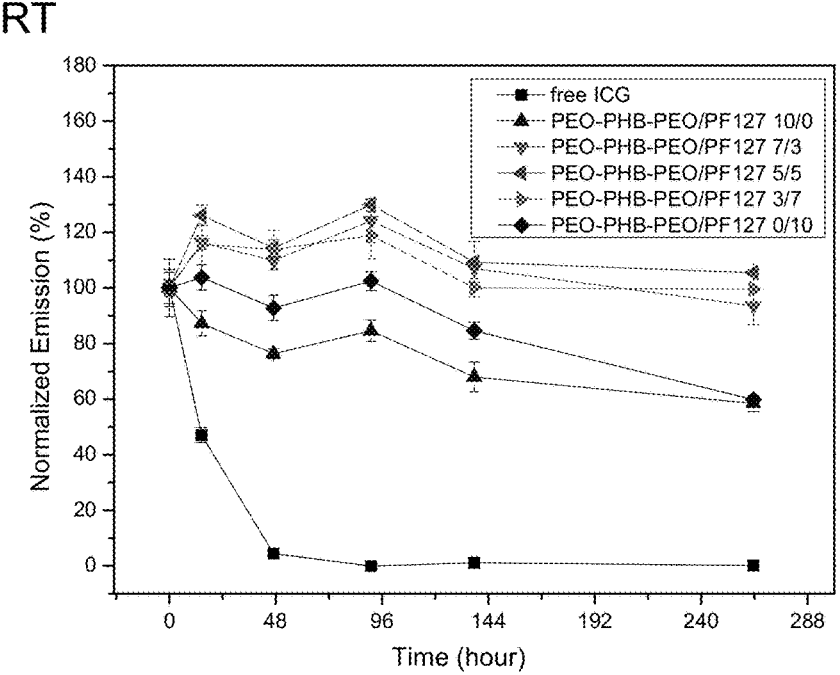
Figure 4B:
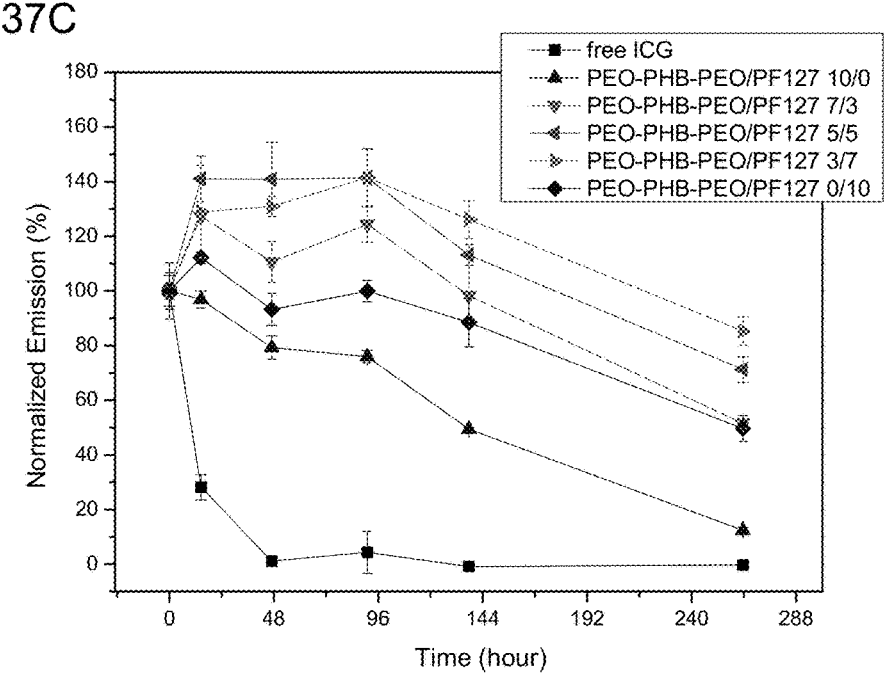

FIGS. 4A and 4B provide fluorescence of indocyanine green (ICG) or ICG-loaded PEO-PHB-PEO: PEO-PPO-PEO mixed micelle formulations suspended in water. FIG. 4A demonstrates ICG fluorescence measured at room temperature. FIG. 4B demonstrates ICG fluorescence measured at 37° C.

Figure 5:
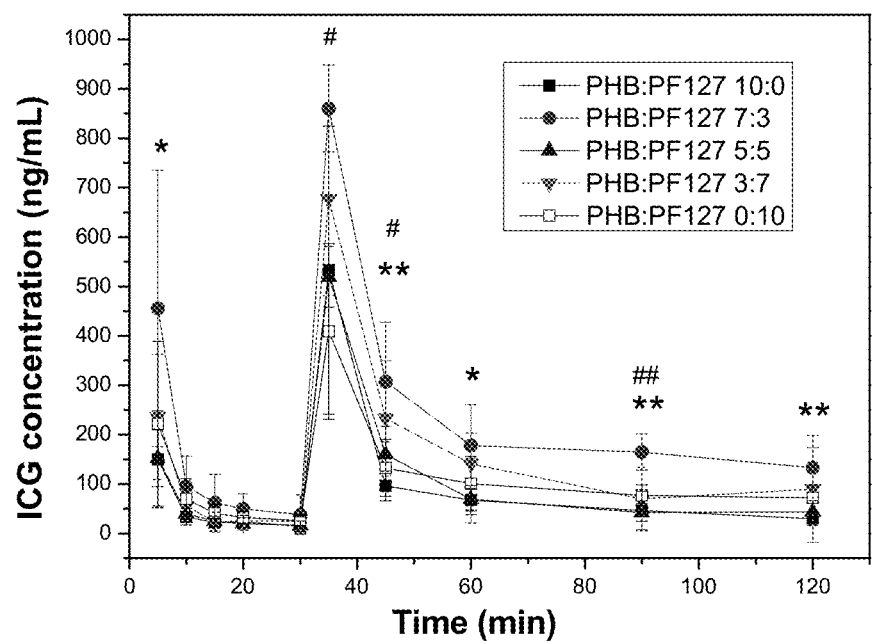

FIG. 5 provides the plasma concentration of ICG over time after intravenous administration of ICG-loaded PEO-PHB-PEO:PEO-PPO-PEO mixed micelle formulations. Statistical analysis was performed using the student's t-test. Symbols * and ** indicate a statistically significant difference of the PEO-PHB-PEO:PEO-PPO-PEO 7:3 formulation from the 10:0 formulation (PEO-PHB-PEO only micelle), $p<0.05$ and $p<0.01$, respectively, n=5. Symbols # and ## indicate a statistically significant difference of the PEO- PHB-PEO:PEO-PPO-PEO 7:3 formulation from the 0:10 (PF-127 only micelle), $p<0.05$ and $p<0.01$, respectively, $n=5$.

Figure 6:
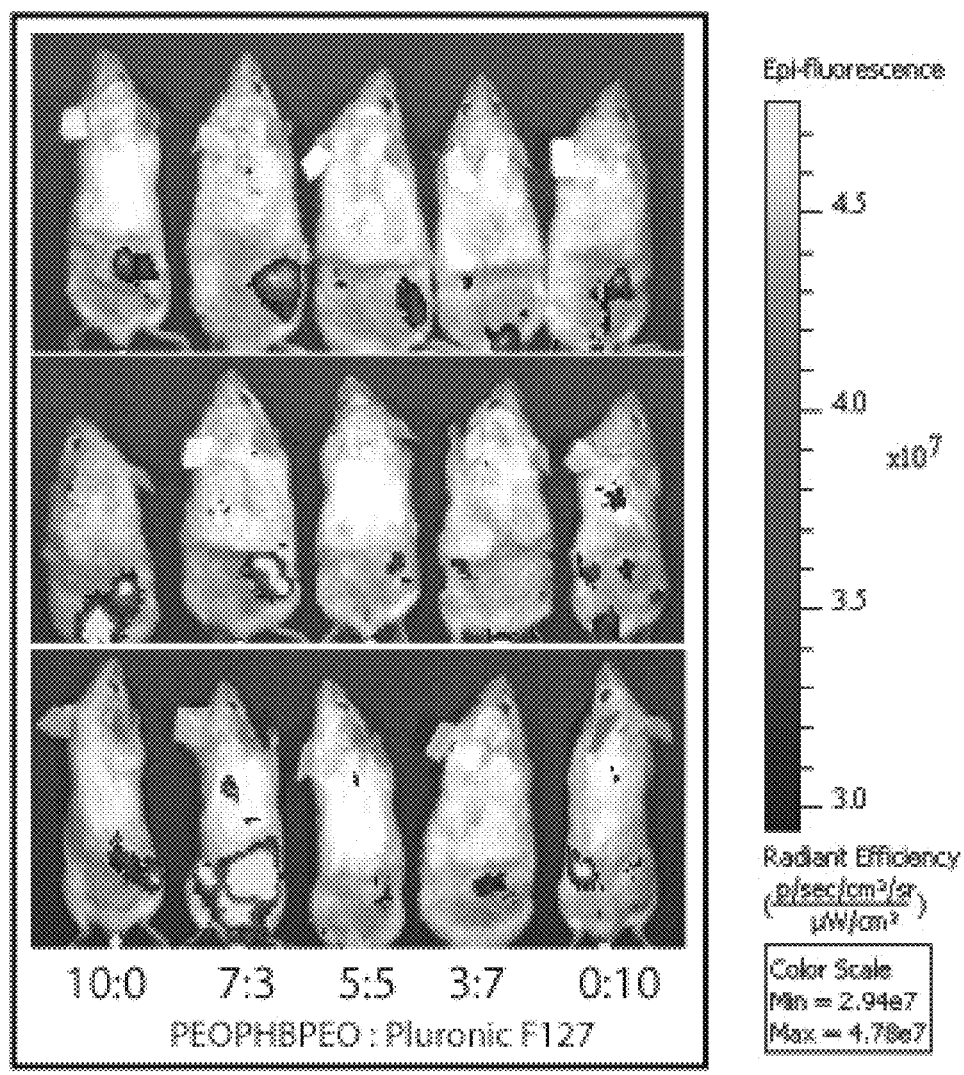

FIG. 6 provides full body images of mice injected with ICG-loaded PEO-PHB-PEO:PEO-PPO-PEO mixed micelles twenty-four hours after initial ICG administration. Images were acquired using a Xenogen Spectrum fluorescence imager, with excitation at 775 nm and emission at 820 nm. All images were scaled to the same minimum and maximum color values.

Figure 7:
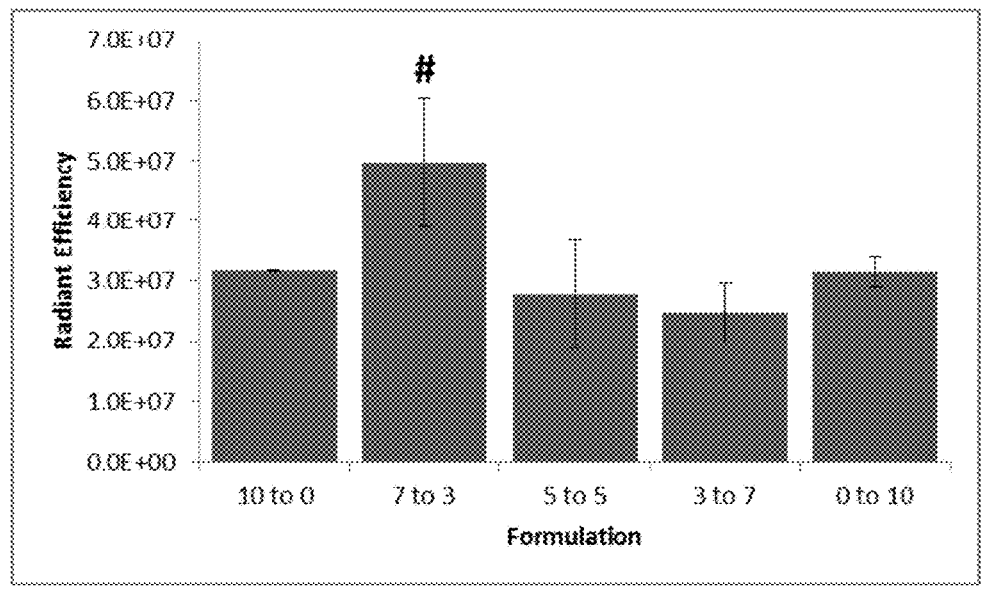

FIG. 7 provides analysis of excised tumor tissues following sacrifice of mice injected with ICG-loaded PEO-PHB-PEO:PEO-PPO-PEO mixed micelles. The amount of ICG fluorescence in tumor tissue excised twenty-four hours after injection was determined using region of interest (ROI) analysis provided by the Living Image® software accompanying the Xenogen Spectrum. The symbol # indicates a statistically significant difference between the 7:3 micelle formulation and both free ICG and the 10:0 micelle formulation (PEO-PHB-PEO only micelle), $p=0.1$, $n=3$.

Figure 8:
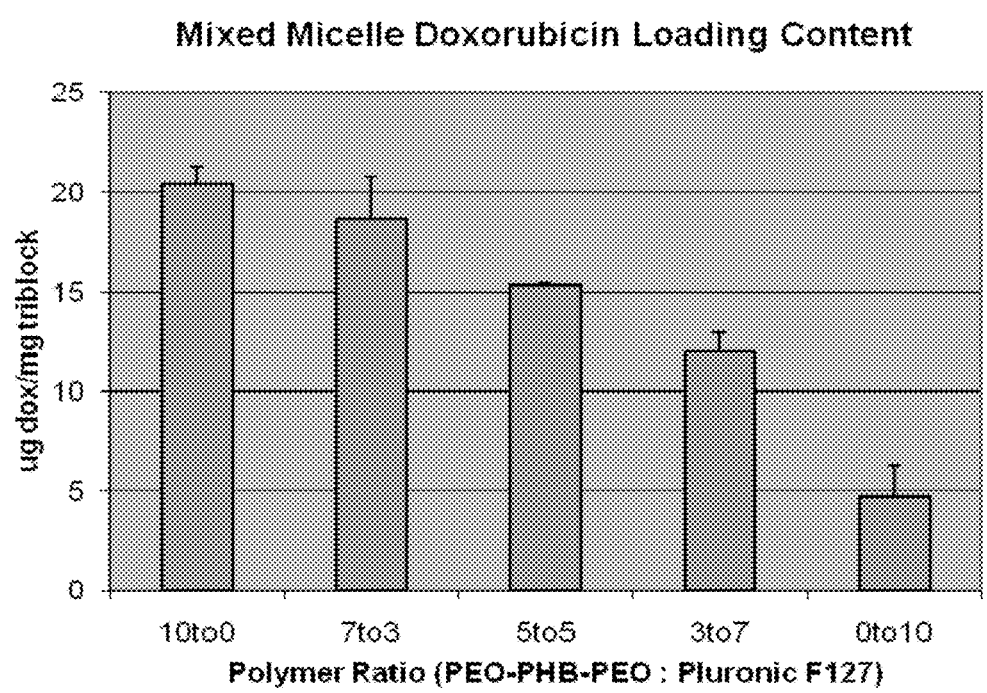

FIG. 8 provides doxorubicin (DOX) loading content measured as mass of encapsulated DOX per mass of polymer in PEO-PHB-PEO:PEO-PPO-PEO mixed micelles.

Figure 9A:
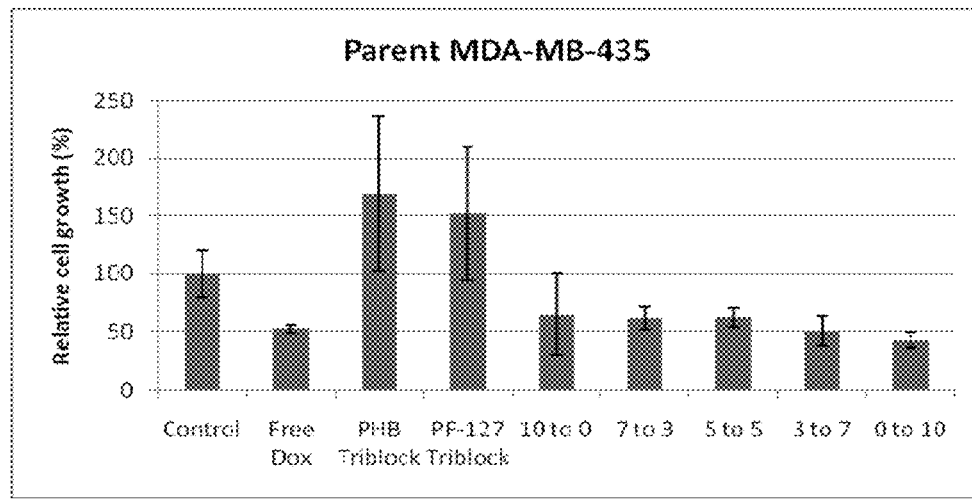
Figure 9B:
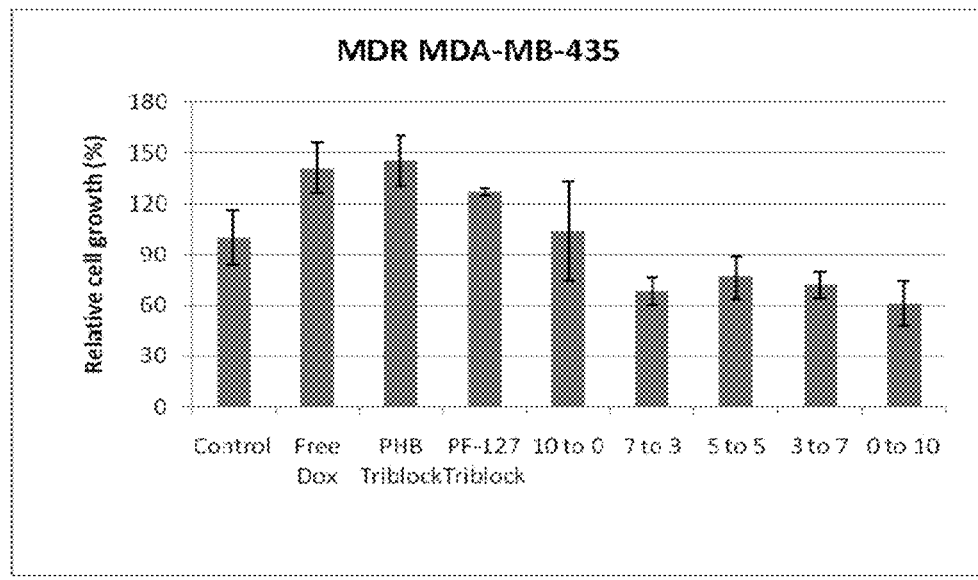

FIGS. 9A and 9B demonstrate cytotoxicity of free DOX and DOX encapsulated in PEO-PHB-PEO:PEO-PPO-PEO mixed micelles. Two cell lines were used. FIG. 9A shows results for the parental cancer cell line: MDA-MB-435. FIG. 9B shows results for the derived multidrug resistant (MDR) cell line: MDR MDA-MB-435.

Figure 10A:
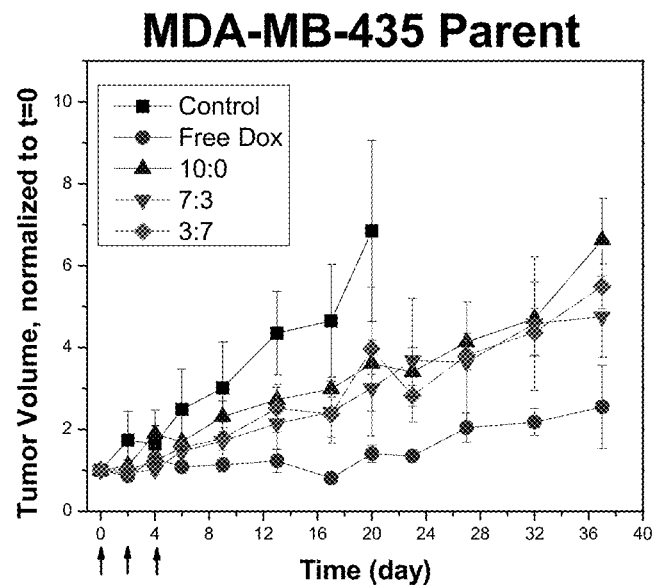
Figure 10B:
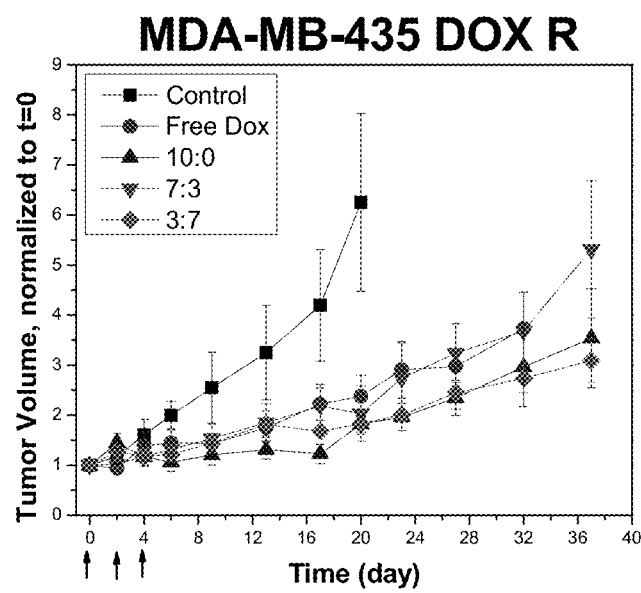

FIGS. 10A and 10B demonstrate tumor suppression by free DOX and DOX encapsulated in PEO-PHB-PEO:PEO-PPO-PEO mixed micelle. Tumors were formed after injection of nude mice with MDA-MB-435 (FIG. 10A) or MDR MDA-MB-435 (FIG. 10B).

Figure 11:
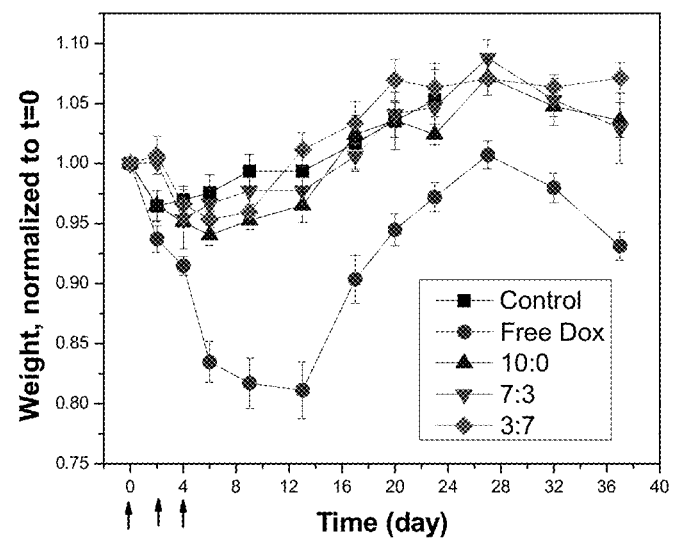

FIG. 11 provides weight fluctuations observed in mice during the tumor reduction study.

V. DETAILED DESCRIPTION OF THE PREFERRED EMBODIMENT

A. Introduction

This disclosure provides for the first time mixed micelles comprising a poloxamer (PEO-PPO-PEO) and a PEO-PHB-PEO triblock copolymer. Such mixed micelles improve properties of encapsulated agents. For example, the mixed micelles of this disclosure enhance stability of indocyanine green (ICG), a dye use in near-infrared (NIR) imaging, increase blood circulation half-life of small molecules such as ICG or doxorubicin (DOX), increase tumor localization of encapsulated agents, reduce systemic toxicity of encapsulated chemotherapeutics, and improve efficacy of drug delivery to drug resistant tumors. The user can also make specific sizes of the mixed micelles, which can influence the biodistribution of micelles in the body of a subject. Certain mixed micelles form filamentous micellar structures, which have also been shown in result in improved tumor delivery.

B. Definitions

The term "PEO-PHB-PEO" is used herein to refer to an amphiphilic copolymer with the general formula A-B-A, wherein the A polymer block is poly(ethylene oxide) (PEO) and the B polymer block is poly[(R)-3-hydroxybutyrate] (PHB). Poly(ethylene oxide) (PEO) is widely used as a hydrophilic and biocompatible polyether. See, e.g., Herold, D. et al., *Biochem. Pharmacol.* 38:73-76 (1989). Poly[(R)-3-hydroxybutyrate] (PHB) is an optically active biodegradable polyester synthesized as a carbon and energy storage material by many microorganisms. See, e.g, Doi, Y. *Microbial Polyesters*; VCH Publisher, New York (1990).

The term "poloxamer" or "PEO-PPO-PEO" is used herein to mean nonionic triblock copolymers composed of a central hydrophobic chain of polyoxypropylene (poly(propylene oxide)) (PPO) flanked by two hydrophilic chains of polyoxyethylene (poly(ethylene oxide)) (PEO). These molecules are also sold under the trade name PLURONIC(S)®. Poloxamers are described in U.S. Pat. No. 3,740,421.

The term "PF-127" is used herein to refer to PLURONIC® F-127 (PEO100-PPO65-PEO100, Mw=12,600).

The term "micelle" is used herein to refer to a structure formed by an amphipathic molecule. In an aqueous solution, the hydrophilic portions of the molecules are on the outside of the structure, in contact with water molecules, while the hydrophobic portions of the molecules are within the structure, sequestered away from water. A "filamentous micelle" as used herein refers to a micelle that has a length that is measureably different than its width, e.g., the micelle is ovate or rod-shaped.

The term "mixed micelle" is used herein to refer to a micelle comprising more than one amphipathic molecule. In one embodiment, a mixed micelle comprises PEO-PHB-PEO and PEO-PPO-PEO molecules, i.e., a PEO-PHB-PEO:PEO-PPO-PEO mixed micelle.

The term "agent" as used herein refers to a compound that has an effect when administered to a subject. The effect can be a physiological or therapeutic effect, e.g., an effect that causes a response in a cell. An effect can be a non-physiological effect, such as allowing visualization of an internal organ or tissue of a subject.

As used herein, the terms "therapeutic agents" and "drugs" are intended to encompass biologically active molecules, including peptides, proteins (e.g., cytokines, growth factors, angiogenesis factors, soluble receptors, antibodies and fragments thereof and human recombinant proteins), small molecules, antisense molecules, small inhibitory RNA molecules (siRNAs), and antigens (e.g., vaccines). The terms "drug" and "therapeutic agent" as used herein are also intended to encompass not only compounds or species that are inherently pharmaceutically or biological active, but also materials which include one or more of these active compounds or species, as well as conjugations, modifications, and pharmacologically active fragments, and antibody derivatives thereof.

The term "chemotherapeutic agent" refers to a drug or agent used to kill growing cells. Chemotherapeutic agents are frequently used to treat various forms of cancer. Examples of chemotherapeutic agents include adriamycin, paclitaxel (Taxol), docetaxel (Taxotere), actinomycin D, doxorubicin, daunorubicin, valrubicin, idarubicin, epirubicin, bleomycin, plicamycin, camptothecin and derivatives, bleomycin, etoposide, teniposide, mitomycin, vinca alkaloids, such as vinblastine and vincristine, and platinum-based compounds such as cisplatin, gemcitabine.

The term "imaging agent" as used herein refers to an agent that can be used to visualize an organ or tissue in a subject. Examples of imaging agents include indocyanine green (ICG), paramagnetic metals such as gadolinium or manganese, iron oxide nanoparticles, quantum dots, and heavy elements such as iodine or barium.

The term "about" is understood to mean that there can be variation in the concentration of a component of the described formulation that can be up to 1%, up to 25, up to 3%, up to 4%, up to 5%, or up to and including 10% of the given value. For example, the phrase "a PEO-PHB-PEO:PEO-PPO-PEO mixed micelle having a ratio of about 7:3" is understood to mean that the ratio can be between 7.7:3.3 and 6.3:2.7.

The term "aqueous solution" as used herein refers to a solution in which the solute is water.

As used herein, "cancer" includes solid tumors and hematological malignancies. The former includes cancers such as breast, colon, and ovarian cancers. The latter include hematopoietic malignancies including leukemias, lymphomas and myelomas. This invention provides new effective methods, compositions, and kits for treatment and/or prevention of various types of cancer.

The terms "tumor" or "solid tumor" or the like refer to an abnormal growth of body tissue. Some tumors are malignant and are caused by uncontrolled growth of cancerous cells. Such tumors may include newly formed blood vessels that respond to angiogenic signals from the cancer cells.

The terms "cancer cell" or "tumor cell" refer to a cell that exhibits uncontrolled growth and division.

The terms "inhibiting cell growth" or "inhibiting cancer cell growth" or "inhibiting tumor growth" or "inhibiting tumor cell growth" or the like, refer to processes of reducing the growth of a cell or population of cells, e.g., in tissue culture or in a mammalian subject. Inhibition of cell growth or cancer cell growth can occur by a decrease in the rate of cell division, by a decrease in the rate of cell growth or proliferation, by delaying cell growth or proliferation, or by an increase in cell death, e.g., an increase in apoptosis.

The terms "multi-drug resistant cancer" or "multi-drug resistant cancer cells" refer to cancer cells whose growth is not inhibited by one or more chemotherapeutic agents. Typically multi-drug resistance develops over time as a chemotherapeutic agent is administered to a subject. Some examples of multi-drug resistant cancer cells include cancer cells that have increased expression or activity of proteins that pump molecules from the interior of a cell to the exterior of a cell. Examples of such proteins are known to those of skill and include, e.g., P-glycoprotein, multidrug resistance-associated protein, lung resistance-related protein, breast cancer resistance protein and reproductive cancer resistance protein.

The term "contacting" is used herein interchangeably with the following: combined with, added to, mixed with, passed over, incubated with, flowed over, etc.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or using antibodies specifically reactive with the peptide for detection.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

By "therapeutically effective dose" herein is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999)).

As used herein, the term "mammalian subject" includes all mammals, including without limitation humans, non-human primates, dogs, cats, horses, sheep, goats, cows, rabbits, pigs, and rodents. The term "non-human mammalian subject" refers to non-human mammals.

C. Components of Mixed Micelles

The mixed micelles of this disclosure comprise at least two amphiphilic molecules: PEO-PHB-PEO and PEO-PPO-PEO.

PEO-PHB-PEO

PEO-PHB-PEO is a copolymer that has been used to form micelles and hydrogels for drug delivery. See, e.g., U.S. Pat. No. 7,297,348 and Kim et al, *Biomat.* 31:7386-7397 (2010). The PEO-PHB-PEO self-assembles into micelles in aqueous solutions at low critical micellar concentrations (CMC). PEO-PHB-PEO is a member of a family of molecules that include an A block and a B block with the general formula ABA. The A polymer block comprises a poly(alkylene oxide) and the B polymer block comprises a poly(hydroxyalkanoate). In one preferred embodiment of the invention, the A polymer block is poly(ethylene oxide) (PEO) and the B polymer block is poly[(R)-3-hydroxybutyrate] (PHB), and the copolymer is the triblock ABA copolymer PEO-PHB-PEO. The A and B block polymer components of the poly(alkylene oxide)-poly(hydroxyalkanoate)-poly(alkylene oxide) copolymers of the present invention will now be described.

A hydrophilic poly(alkylene oxide) end segment structure (the A block polymer) is used in the triblock copolymers of the present invention. The poly(alkylene oxide) is suitably selected from poly(ethylene oxide), poly(tetramethylene oxide) and poly(tetrahydrofuran). A preferred poly(alkylene oxide) for use in the present invention is poly(ethylene oxide) (PEO) or a derivative thereof, and most preferably is PEO. PEO is also referred to as poly(ethylene glycol), and as used herein the term poly(ethylene oxide) (and the abbreviation PEO) is intended to also refer to poly(ethylene glycol) (PEG).

The poly(alkylene oxide) may have different forms and different end groups. For example, in the case of PEO, the PEO derivatives may have different structures, e.g. star-shaped PEO, comb-like PEO, etc. The poly(ethylene oxide) may be in the form of modified molecules, e.g. PEGylated polysaccharides, PEGylated poly(amino acid)s, PEGylated proteins, etc. In addition, a polyamine derivative of PEO, e.g. PEGylated poly(ethylene imine) or PEGylated polylysine, may be used.

The relative molecular mass (Mr) range of PEO or other poly(alkylene oxide) utilized as the A block polymer in the copolymers of the present invention is suitably 500 to 20,000, and preferably is 2,000 to 10,000.

A highly hydrophobic poly(hydroxyalkanoate) midsection structure (B block polymer) is used in the triblock copolymers of the present invention. Suitable poly(hydroxyalkanoate)s are: a) relatively hydrophobic so the hydrophobic-hydrophobic interaction between the polymer chains facilitates the macromolecular assembly and reduces the concentration of CD needed; b) biodegradable; and c) non-toxic and biocompatible.

Suitable hydrophobic B polymer blocks for use in the present invention are poly(hydroxyalkanoate)s. Examples of suitable poly(hydroxyalkanoate)s for use in the present invention include: poly[(R)-3-hydroxybutyrate] (PHB), also referred to as poly[(R)-3-hydroxybutryic acid] or poly (.beta.-hydroxy acid); poly[(R)-4-hydroxybutyrate] (PGHB); poly[(R)-3-hydroxyvalerate] (PHV); poly[(R)-3-hydroxybutyrate]-co-poly[(R)-3-hydroxyvalerate] (PHB/HV); poly[(R)-3-hydroxyhexanoate] (PHHx); poly[(R)-3-hydroxyheptanoate] (PHHp); (S) enantiomers of each of the above (R) enantiomers; racemic mixtures of the above (S) and (R) enantiomers; and mixtures of the above poly(hydroxyalkanoate)s. Preferred poly(hydroxyalkanoate)s are poly (β-hydroxy alkanoate)s, and more specifically are poly [(R)-3-hydroxybutyrate] (PHB) and related poly[(R)-3-hydroxyalkanoate]s. A most preferred poly(hydroxyalkanoate) for use in the present invention is PHB.

Poloxamers

Poloxamers, trade name PLURONICS™, are a series of water-soluble block copolymers, composed of two polyoxyethylene blocks separated by a polyoxypropylene block. Poloxamers have the general structure of PEO-PPO-PEO. The ability of poloxamers to form micelles and gels makes them an important class of surfactant, that find widespread use in industrial applications such as detergency, dispersion stabilization, foaming, emulsification, lubrication and formation of cosmetics and inks. The amphiphilic property of poloxamers is the reason for their ability to create micelles above the CMC (critical micellization concentration) and the CMT (critical micellization temperature). The micellization of block copolymers, as in the case of conventional surfactants, obeys the closed association model, which assumes equilibrium between molecularly disposed copolymer (unimer) and multimolecular aggregates (micelles). In the case of poloxamers, when micellization occurs the degree of structuring of the water molecules is decreased. The hydrogen bonding structure in the water is restored and the water entropy increases, overcoming the entropy loss due to the localization of the hydrophobic chains in the micelles. The structure of the poloxamer micelles in water has been investigated in many studies. In general, the unimer size is found to be approximately 1 nm and the micelle size 10 nm, independent of copolymer concentration.

The water solution block copolymers of poly(ethylene ocide)-poly(propylene oxide)-poly(ethylene oxide) which are commercially available (ICI company) and (Basf company). Some examples of poloxamers or PLURONICS for use in the invention are: F-127, F-108, F-98, F-88, F-68, F-87, F-77, P-105, P-85, P-75, P-65, P-104, P-94, P-84, L-64, L-63, L-121, and L-122.

D. Formation and Properties of Mixed Micelles

Mixed micelles self-assemble by combining a desired formulation of PEO-PHB-PEO and PEO-PPO-PEO at concentrations above the critical micellar concentration. For most purposes micelles are loaded with an agent of interest, e.g., an imaging agent or a therapeutic agent.

In some embodiments, mixed micelle formulations are a combination of a PEO-PHB-PEO polymer and a PEO-PPO-PEO polymer at a desired ratio. In other embodiments, mixed micelle formulations are a combination of a PEO-PHB-PEO polymer and two or more PEO-PPO-PEO polymers at a desired ratio. One or more PEO-PPO-PEO polymers can be selected from the following commercially available PLURONIC polymers: F-127, F-108, F-98, F-88, F-68, F-87, F-77, P-105, P-85, P-75, P-65, P-104, P-94, P-84, L-64, L-63, L-121, and L-122.

In some embodiments, the agent to be encapsulated in a mixed micelle is insoluble in an aqueous solution. Micelles loaded with a water insoluble agent are made by a variety of methods, e.g., dialysis, emulsification or solvent evaporation, and film methods. In the dialysis method, the agent and PEO-PHB-PEO/PEO-PPO-PEO formulation are dissolved in a water miscible solvent, e.g., ethanol, and then dialyzed against an aqueous solution. During the dialysis, which can take several days, the insoluble agent is incorporated into the micellar core. In the emulsification method, an oil:water emulsion is prepared using an aqueous solution of PEO-PHB-PEO/PEO-PPO-PEO and the agent in a water insoluble volatile solvent, such as chloroform. The agent loaded micelle is formed as the solvent evaporates. In the film method, the PEO-PHB-PEO/PEO-PPO-PEO and the agent are dissolved separately in miscible volatile organic solvents, which are then mixed. The solvents are then evaporated to form a PEO-PHB-PEO/PEO-PPO-PEO-agent film. The film is hydrated in an aqueous solution and micelles are formed by vigorous shaking.

In one embodiment, a formulation of PEO-PHB-PEO/PEO-PPO-PEO is prepared in an aqueous solution, while the agent is prepared in a water insoluble volatile solvent. The two are mixed to form an emulsion and then the solvent is evaporated off to form the micelles. This method of micelle synthesis does not require extreme physical manipulations, such as sonication or heating, to assist formation of the micelles.

In one embodiment, a formulation of PEO-PHB-PEO/PEO-PPO-PEO is prepared in an aqueous solution, while a therapeutic agent is prepared in a water insoluble volatile solvent. The two are mixed to form an emulsion and then the solvent is evaporated off to form the micelles. This method of micelle synthesis does not require extreme physical manipulations, such as sonication or heating, to allow formation of the micelles.

In one embodiment, a formulation of PEO-PHB-PEO/PEO-PPO-PEO is prepared in an aqueous solution, while a chemotherapeutic agent, e.g., doxorubicin, paclatoxin, adriamycin, docetaxel (Taxotere), actinomycin D, daunorubicin, valrubicin, idarubicin, epirubicin, bleomycin, plicamycin, camptothecin and derivatives, bleomycin, etoposide, teniposide, mitomycin, vinca alkaloids, such as vinblastine and vincristine, or platinum-based compounds such as cisplatin, gemcitabine, is prepared in a water insoluble volatile solvent. The two are mixed to form an emulsion and then the solvent is evaporated off to form the micelles. This method of micelle synthesis does not require extreme physical manipulations, such as sonication or heating, to assist formation of the micelles.

In one embodiment, a formulation of PEO-PHB-PEO/PEO-PPO-PEO is prepared in an aqueous solution, while an imaging agent is prepared in a water insoluble volatile solvent. The two are mixed to form an emulsion and then the solvent is evaporated off to form the micelles. This method of micelle synthesis does not require extreme physical manipulations, such as sonication or heating, to assist formation of the micelles.

In one embodiment, a formulation of PEO-PHB-PEO/PEO-PPO-PEO is prepared in an aqueous solution, while an imaging agent, e.g., ICG, paramagnetic metals such as gadolinium or manganese, iron oxide nanoparticles, quantum dots, or heavy elements such as iodine or barium, is prepared in a water insoluble volatile solvent. The two are mixed to form an emulsion and then the solvent is evaporated off to form the micelles. This method of micelle synthesis does not require extreme physical manipulations, such as sonication or heating, to assist formation of the micelles.

Formulations of mixed micelles are typically expressed as molar ratios of PEO-PHB-PEO to PEO-PPO-PEO. In one embodiment, the mixed micelle ratio of PEO-PHB-PEO to PEO-PPO-PEO is 7:3. In one embodiment, the mixed micelle ratio of PEO-PHB-PEO to PEO-PPO-PEO is 5:5. In one embodiment, the mixed micelle ratio of PEO-PHB-PEO to PEO-PPO-PEO is 3:7. In one embodiment, the mixed micelle ratio of PEO-PHB-PEO to PEO-PPO-PEO is 10:0. In one embodiment, the mixed micelle ratio of PEO-PHB-PEO to PEO-PPO-PEO is 9:1. In one embodiment, the mixed micelle ratio of PEO-PHB-PEO to PEO-PPO-PEO is 8:2. In one embodiment, the mixed micelle ratio of PEO-PHB-PEO to PEO-PPO-PEO is 6:4. In one embodiment, the mixed micelle ratio of PEO-PHB-PEO to PEO-PPO-PEO is 4:6. In one embodiment, the mixed micelle ratio of PEO-PHB-PEO to PEO-PPO-PEO is 2:8. In one embodiment, the mixed micelle ratio of PEO-PHB-PEO to PEO-PPO-PEO is 1:9.

In further embodiments, the mixed micelle ratio of PEO-PHB-PEO to PEO-PPO-PEO is about 7:3. In another embodiment, the mixed micelle ratio of PEO-PHB-PEO to PEO-PPO-PEO is about 5:5. In another embodiment, the mixed micelle ratio of PEO-PHB-PEO to PEO-PPO-PEO is about 3:7. In another embodiment, the mixed micelle ratio of PEO-PHB-PEO to PEO-PPO-PEO is about 10:0. In another embodiment, the mixed micelle ratio of PEO-PHB-PEO to PEO-PPO-PEO is about 9:1. In another embodiment, the mixed micelle ratio of PEO-PHB-PEO to PEO-PPO-PEO is about 8:2. In another embodiment, the mixed micelle ratio of PEO-PHB-PEO to PEO-PPO-PEO is about 6:4. In another embodiment, the mixed micelle ratio of PEO-PHB-PEO to PEO-PPO-PEO is about 4:6. In another embodiment, the mixed micelle ratio of PEO-PHB-PEO to PEO-PPO-PEO is about 2:8. In another embodiment, the mixed micelle ratio of PEO-PHB-PEO to PEO-PPO-PEO is about 1:9.

Poloxamers, including PEO-PPO-PEO, are thermosensitive molecules. Some poloxamers, such as PLURONIC™ F127 (PF-127), do not form micelles at room temperature. However, at physiological temperature, e.g, about 37° C., PEO-PPO-PEO molecules form micelles with a diameter of about 26 nm. Mixed micelles comprising PEO-PHB-PEO and PEO-PPO-PEO also exhibit temperature sensitive changes in diameter. At 25° C., the effective diameters of ICG-loaded PEO-PHB-PEO:PEO-PPO-PEO mixed micelles are between 107-114 nm. See, e.g., Example 1, herein. At 37° C., the effective diameter of the PEO-PHB-PEO/PEO-PPO-PEO mixed micelles varies with the amount of PEO-PPO-PEO in the mixed micelle. At 37° C., micelles comprising only PEO-PHB-PEO have an effective diameter of about 118 nm; mixed micelles with a PEO-PHB-PEO:PEO-PPO-PEO ratio of 7:3 have an effective diameter of about 110 nm; mixed micelles with a PEO-PHB-PEO:PEO-PPO-PEO ratio of 5:5 have an effective diameter of about 99 nm; mixed micelles with a PEO-PHB-PEO:PEO-PPO-PEO ration of 3:7 have an effective diameter of about 81 nm. Thus, this disclosure provides PEO-PHB-PEO:PEO-PPO-PEO mixed micelles of defined sizes and methods to make such micelles.

In one embodiment, a PEO-PHB-PEO:PEO-PPO-PEO mixed micelle has an effective diameter of about 110 nm at physiological temperature, e.g., 35° C.-39° C. In one embodiment, a PEO-PHB-PEO:PEO-PPO-PEO mixed micelle has an effective diameter of about 99 nm at physiological temperature, e.g., 35° C.-39° C. In another embodiment, a PEO-PHB-PEO:PEO-PPO-PEO mixed micelle has an effective diameter of about 81 nm at physiological temperature, e.g., 35° C.-39° C. In a further embodiment, a PEO-PHB-PEO:PEO-PPO-PEO mixed micelle has an effective diameter of about 110 nm at physiological temperature, e.g., 35° C.-39° C.

In one embodiment, a PEO-PHB-PEO:PEO-PPO-PEO mixed micelle that has an effective diameter of about 99 nm at physiological temperature is made by combining PEO-PHB-PEO and PEO-PPO-PEO in a ratio of about 5:5 at a concentration above the CMC. In another embodiment, a PEO-PHB-PEO:PEO-PPO-PEO mixed micelle that has an effective diameter of about 81 nm at physiological temperature is made by combining PEO-PHB-PEO and PEO-PPO-PEO in a ratio of about 3:7 at a concentration above the CMC. In a further embodiment, a PEO-PHB-PEO:PEO-PPO-PEO mixed micelle that has an effective diameter of about 110 nm at physiological temperature is made by combining PEO-PHB-PEO and PEO-PPO-PEO in a ratio of about 7:3 at a concentration above the CMC.

E. Uses of PEO-PHB-PEO:PEO-PPO-PEO Mixed Micelles

The PEO-PHB-PEO:PEO-PPO-PEO mixed micelles of the disclosure can be used to administer a variety of agents to a subject. For example, in one embodiment, the PEO-PHB-PEO:PEO-PPO-PEO mixed micelles can be used to administer an imaging agent to assist a physician in visualizing a tissue, organ, or structure in a subject. In another embodiment, the PEO-PHB-PEO:PEO-PPO-PEO mixed micelles can be used to administer a therapeutic agent to treat a disease or disorder in a subject.

The PEO-PHB-PEO:PEO-PPO-PEO mixed micelles of this disclosure can be used to administer hydrophobic drugs and imaging agents that would not otherwise be compatible with the aqueous nature of the physiological environment of a subject. In addition, some agents are rapidly degraded in the physiological environment and, thus, PEO-PHB-PEO:PEO-PPO-PEO mixed micelles of this disclosure can be used to reduce the degradation or denaturation of susceptible therapeutic agents and imaging agents.

PEO-PHB-PEO:PEO-PPO-PEO mixed micelles of a size between about 10 and about 120 nm are able to avoid uptake by macrophages of the reticuloendothelial system (RES). Thus, PEO-PHB-PEO:PEO-PPO-PEO mixed micelles of a size between about 10 and about 120 nm are used to enhance the bioavailability of therapeutic or imaging agents.

The PEO-PHB-PEO:PEO-PPO-PEO mixed micelles of a size between about 10 and about 120 nm are also used to target imaging agents or therapeutic agents to tumors, either benign or malignant. In order for tumor cells to grow quickly, particularly cancerous tumor cells, blood vessels must be generated to bring nutrients and oxygen to the tumor cells. Angiogenesis is stimulated at the tumor by the release of VEGF and other growth factors. The newly formed tumor blood vessels are usually abnormal in form and architecture with wide fenestrations, lacking a smooth muscle layer, or innervation and having a wider lumen. In addition, tumor tissues usually lack effective lymphatic drainage. The larger openings between the tumor blood vessels and the tumor cells allows preferential uptake of particles of a size between about 10 and about 120 nm. This phenomenon is the "enhanced permeability and retention (EPR)-effect" of solid tumors.

In one embodiment, PEO-PHB-PEO:PEO-PPO-PEO mixed micelles of a size between 10 and 100 nm are used to target an imaging agent to a solid tumor. In another embodiment, PEO-PHB-PEO:PEO-PPO-PEO mixed micelles of a size between about 10 and about 120 nm are used to target a therapeutic agent to a solid tumor. In a further embodiment, PEO-PHB-PEO:PEO-PPO-PEO mixed micelles of a size between about 10 and about 120 nm are used to target a chemotherapeutic agent to a solid tumor.

In one embodiment, filamentous PEO-PHB-PEO:PEO-PPO-PEO mixed micelles are used to target an imaging agent to a solid tumor. In another embodiment, filamentous PEO-PHB-PEO:PEO-PPO-PEO mixed micelles are used to target a therapeutic agent to a solid tumor. In a further embodiment, filamentous PEO-PHB-PEO:PEO-PPO-PEO mixed micelles are used to target a chemotherapeutic agent to a solid tumor.

Delivery of Chemotherapeutic Agents

In one embodiment, the PEO-PHB-PEO:PEO-PPO-PEO mixed micelles disclosed herein are used to administer a chemotherapeutic agent to a subject in need of such treatment. In another embodiment, the PEO-PHB-PEO:PEO-PPO-PEO mixed micelles disclosed herein are used to administer a chemotherapeutic agent to a subject with a solid tumor. In a further embodiment, the PEO-PHB-PEO:PEO-PPO-PEO mixed micelles disclosed herein are used to administer a chemotherapeutic agent to a subject with a solid tumor and the PEO-PHB-PEO:PEO-PPO-PEO mixed micelles are of a size to be preferentially taken up by the cells of the solid tumor as compared to cell outside the tumor. In a further embodiment, the PEO-PHB-PEO:PEO-PPO-PEO mixed micelles disclosed herein are used to administer a chemotherapeutic agent to a subject with a solid tumor and the PEO-PHB-PEO:PEO-PPO-PEO mixed micelles are of a shape, e.g., a filamentous shape, to be preferentially taken up by the cells of the solid tumor as compared to cell outside the tumor. In another embodiment, the PEO-PHB-PEO:PEO-PPO-PEO mixed micelles disclosed herein are used to administer a chemotherapeutic agent to a subject with a solid tumor and some or all of the tumor cells are multidrug resistant (MDR).

In one embodiment, the PEO-PHB-PEO:PEO-PPO-PEO mixed micelles disclosed herein are used to administer a chemotherapeutic agent that is a small molecule. In one embodiment, the PEO-PHB-PEO:PEO-PPO-PEO mixed micelles disclosed herein are used to administer a chemotherapeutic agent that is a member of the group consisting of adriamycin, paclitaxel (Taxol), docetaxel (Taxotere), actinomycin D, doxorubicin, daunorubicin, valrubicin, idarubicin, epirubicin, bleomycin, plicamycin, and mitomycin. In one embodiment, the PEO-PHB-PEO:PEO-PPO-PEO mixed micelles disclosed herein are used to administer a chemotherapeutic agent that is an antisense molecule or an siRNA molecule directed against a nucleic acid that is expressed by the cells of the tumor. In one embodiment, the PEO-PHB-PEO:PEO-PPO-PEO mixed micelles disclosed herein are used to administer a chemotherapeutic agent that is an antibody that specifically binds to a protein expressed by the cells of the tumor. In one embodiment, the PEO-PHB-PEO:PEO-PPO-PEO mixed micelles disclosed herein are used to administer a chemotherapeutic agent that is a gold nanoparticle.

Delivery of Imaging Agents

In one embodiment, the PEO-PHB-PEO:PEO-PPO-PEO mixed micelles disclosed herein are used to administer an imaging agent to assist a physician in visualizing a tissue, organ, or structure in a subject. In another embodiment, the PEO-PHB-PEO:PEO-PPO-PEO mixed micelles disclosed herein are used to administer an imaging agent to a subject with a solid tumor in order to visualize the tumor. In a further embodiment, the PEO-PHB-PEO:PEO-PPO-PEO mixed micelles disclosed herein are used to administer an imaging agent to a subject with a solid tumor and the PEO-PHB-PEO:PEO-PPO-PEO mixed micelles are of a size to be preferentially taken up by the cells of the solid tumor as compared to cell outside the tumor.

In one embodiment, the PEO-PHB-PEO:PEO-PPO-PEO mixed micelles disclosed herein are used to administer an imaging agent that is visualized using near infrared imaging technique. In a further embodiment, the imaging agent is indocyanine green. Other embodiments include use of the imaging agents including paramagnetic metals such as gadolinium or manganese, iron oxide nanoparticles, quantum dots, and heavy elements such as iodine or barium. Magnetic resonance imaging (MRI) can be performed using, e.g., paramagnetic gadolinium delivered via the mixed micelles described herein.

Delivery of Therapeutic Agents

The PEO-PHB-PEO:PEO-PPO-PEO mixed micelles disclosed herein can also be used to deliver a wide variety of therapeutic agents to subjects in need of treatment of a disease or disorder. The therapeutic agents are encapsulated in the PEO-PHB-PEO:PEO-PPO-PEO mixed micelles which are then suspended in a suitable pharmaceutical carrier. The therapeutic agent(s) may be any drug suitable for injection or other mode of delivery, or combinations of such drugs. Suitable drugs include, but are not limited to, analgesics, anesthetics, anti-arthritic drugs, disease modifying anti-rheumatic drugs (DMARDS), anti-asthma drugs, anticoagulants, anticonvulsants, antidepressants, antidiabetics, antipsychotics, antihypertensives, antibiotics, antihistamines, decongestants, anti-inflammatories, muscle relaxants, anti-parasitic drugs, antiviral drugs, anti-restenotic agents, anti-spasm agents, chondroprotective agents, anti-adhesion agents, anti-tumor cell invasion agents, vasorelaxants, vasoconstrictors, immunosupressants and other biologically active molecules, including peptides, proteins (e.g., cytokines, growth factors, angiogenesis factors, soluble receptors, antibodies and fragments thereof and human recombinant proteins), small molecules, antigens (e.g., vaccines), antisense RNA, and siRNA molecules.

F. Dosage and Administration

The PEO-PHB-PEO:PEO-PPO-PEO mixed micelles of the present invention may be administered to a subject as a pharmaceutical composition or formulation. In particular embodiments, pharmaceutical compositions of the present invention may be in any form which allows for the composition to be administered to a subject. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, epidural, intrasternal injection or infusion techniques.

Pharmaceutical compositions used according to the present invention comprise a PEO-PHB-PEO:PEO-PPO-PEO mixed micelle, typically with an encapsulated agent, and a pharmaceutically acceptable diluent, excipient, or carrier. "Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate buffered saline at physiological pH may be used. Preservatives, stabilizers, dyes and even flavoring agents may be provided in the pharmaceutical composition. For example, sodium benzoate, sorbic acid and esters of p hydroxybenzoic acid may be added as preservatives. Id. at 1449. In addition, antioxidants and suspending agents may be used. Id. Appropriate pharmaceutical carriers include, e.g., phosphate-buffered saline (PBS), 5% glucose, or other physiological buffers, such as tris, citrate, acetate, succinate, or histidine buffers.

The pharmaceutical preparation comprising a PEO-PHB-PEO:PEO-PPO-PEO mixed micelle is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders or liquids in vials or ampoules. Also, the unit dosage form can be a capsule, tablet, cachet, or lozenge itself, or it can be the appropriate number of any of these in packaged form.

The PEO-PHB-PEO:PEO-PPO-PEO mixed micelles (in the form of their compositions) are administered to patients by the usual means known in the art, for example, orally or by injection, infusion, infiltration, irrigation, inhalation, topical delivery and the like.

Routes and frequency of administration of the PEO-PHB-PEO:PEO-PPO-PEO mixed micelles described herein, as well as dosage, will vary from individual to individual, and may be readily established using standard techniques. Preferably, between 1 and 100 doses may be administered over a 52-week period. A suitable dose is an amount of PEO-PHB-PEO:PEO-PPO-PEO mixed micelle that, when administered as described above, has a beneficial therapeutic effect.

In general, an appropriate dosage and treatment regimen provides the active therapeutic agent or imaging agent in an amount sufficient to provide therapeutic benefit or a usable image. Therapeutic benefit can be monitored by establishing an improved clinical outcome (e.g., more frequent remissions, complete or partial, or longer disease-free survival) in treated patients as compared to non-treated patients. Imaging can be monitored by appropriate means, e.g., MR.

A therapeutic amount of a PEO-PHB-PEO:PEO-PPO-PEO mixed micelle comprising a therapeutic agent as described in this application, means an amount effective to yield the desired therapeutic response, for example, an amount effective to delay the growth of a cancer or to cause a cancer to shrink or not metastasize.

Patients that can be treated with a PEO-PHB-PEO:PEO-PPO-PEO mixed micelle described in this application, include, for example, patients that have been diagnosed as having squamous cell carcinoma, lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

Within such methods, pharmaceutical compositions comprising PEO-PHB-PEO:PEO-PPO-PEO mixed micelles are typically administered to a patient. As used herein, a "patient" or a "subject" refers to any warm-blooded animal, preferably a human. A patient may or may not be afflicted with solid tumor or other malignancy. Accordingly, the above pharmaceutical compositions may be used to prevent the development of a solid tumor or other malignancy, or delay its appearance or reappearance, or to treat a patient afflicted with a solid tumor or other malignancy. A solid tumor or other malignancy may be diagnosed using criteria generally accepted in the art. Pharmaceutical compositions comprising PEO-PHB-PEO:PEO-PPO-PEO mixed micelles may be administered either prior to or following surgical removal of primary solid tumors and/or treatment such as administration of radiotherapy or conventional chemotherapeutic drugs, or bone marrow transplantation (autologous, allogeneic or syngeneic).

The PEO-PHB-PEO:PEO-PPO-PEO mixed micelles comprising a therapeutic agent or an imaging agent provided herein may be used alone or in combination with conventional therapeutic regimens such as surgery, irradiation, chemotherapy and/or bone marrow transplantation (autologous, syngeneic, allogeneic or unrelated).

Kits for administering the PEO-PHB-PEO:PEO-PPO-PEO mixed micelles may be prepared containing a composition or formulation of the PEO-PHB-PEO:PEO-PPO-PEO mixed micelle comprising a therapeutic agent or an imaging agent, together with the customary items for administering the therapeutic ingredient.

It must be noted that as used herein and in the appended claims, the singular forms "a", "and", and "the" include plural referents unless the context clearly dictates otherwise. Thus, for example, reference to "a mixed micelle" includes a plurality of such micelles and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All citations are incorporated herein by reference.

EXAMPLES

Experiment 1

Synthesis and Characterization of PEO-PHB-PEO/PEO-PPO-PEO Mixed Micelles

Materials

Natural source poly[(R)-3-hydroxy butyrate] (MB), anhydrous diethylene glycol dimethyl ether (diglyme), anhydrous ethylene glycol, dibutyltin dilaurate, 4-(dimethylamino) pyridine (DMAP), triethylamine, and anhydrous dichloromethane were purchased from Sigma Aldrich (St. Louis, Mo.). Methoxy-poly (ethylene glycol)-monocarboxylic acid (mPEG-COOH, Mw 4900) and fluorenylmethyloxycarbonyl-PEG-monocarboxylic acid (Fmoc-PEG-COOH, Mw 4200) were obtained from Laysan Bio (Arab, Ala.). Doxorubicin hydrochloride (DOX-HCl) was obtained from Fisher Scientific (Pittsburgh, Pa.). Pluronic F-127 (PE0100-PP065-PE0100, Mw=12,600) and indocyanine green (ICG), were purchased from Sigma-Aldrich (St. Louis, Mo., USA). Tetrabutylammonium iodide (TBAI) and 1,3-N,N'-dicyclohexylcarbodiimide (DCC) were purchased from Acros Organics (Morris Plains, N.J.) and MP Biomedicals (Lolon, Ohio) respectively. Solvents used were ACS grade and obtained from J. T. Baker Chemical Co. (Phillipsburg, N.J.) with the exception of chloroform (EMD, Gibbstown, N.J.).

Synthesis of PEO-PHB-PEO Triblock Copolymers

PEO-PHB-PEO triblock copolymers were synthesized as previously described. See, e.g., Kim, et al., Biomaterials 31:7386-7397 (2010) and Hirt, et al., *Macromolecular Chemistry and Physics*, 197:1609-1614 (1996). Briefly, PHB diol with a molecular weight of 2300 kDa (Mw 2300) was prepared from purified natural high molecular weight PHB by transesterification with diethylene glycol using dibutyltin dilaurate as a catalyst in diglyme. PEO-PHB-PEO copolymers were then synthesized as previously described. See, e.g., Li, et al., Macromolecules 36:2661-2667 (2003) and Li, et al., J. Physical Chemistry B 110:5920-5926 (2006). Following fractional precipitation from a mixed solvent of chloroform/diethyl ether, the triblock copolymer was purified by filtration through Amicon regenerated cellulose membranes (molecular weight cutoff 30 kDa, Millipore, Billerica, Mass.). Purity was subsequently confirmed by NMR and GPC analysis.

Preparation of ICG-Encapsulating Mixed Micelles

ICG-encapsulated micelles were prepared by solvent evaporation using PEO-PHB-PEO, PF-127 (the PEO-PPO-PEO molecule used in these studies), or mixtures of these two polymers. A solvent evaporation method was implemented to encapsulate ICG within micelles after complexing ICG with TBAI to form a hydrophobic ICG-tetrabutylamine salt, as previously described. See, e.g., Rodriguez, et al., *J. Biomedical Optics* 13(1) (2008). Initially, a 1 mM ICG solution was prepared in chloroform with a six-fold molar excess of TBAI. After sonication for thirty minutes, the ICG solution was added dropwise to stirring micelle solutions containing various ratios of PHB triblock (PEO-PHB-PEO) to Pluronic F127 triblock (PEO-PPO-PEO) (10:0, 7:3, 5:5, 3:7, 0:10). The chloroform was evaporated off to incorporate ICG into the hydrophobic cores of mixed micelles. Free ICG was removed using Amicon regenerated cellulose centrifuge filters (MWCO 10 kDa000, Millipore, Billerica, Mass.), and the remaining ICG-loaded micelle solution was rinsed two times using deionized (DI) water. Purified micelles were resuspended in the original volume of DI water, and lyophilized using a Labconco FreeZone 2.5 benchtop freeze dryer (Labconco, Kansas City, Mo.).

ICG Loading Efficiency and ICG Content

Lyophilized micelles were weighed and dissolved in 1 mL of dimethyl sulfoxide (DMSO), causing complete dissolution of the micelle and release of the encapsulated ICG. Empty micelles dissolved in DMSO were used as a blank for ICG/ICG-loaded micelle samples. The ICG concentration was determined by comparing absorbance at 775 nm to a standard curve of ICG with a squared correlation coefficient of 0.999 in the linear range of 0-12.5 μM in DMSO. ICG content was expressed as the weight ratio between loaded ICG and total weight of ICG-loaded micelle, and loading efficiency as the weight percent of encapsulated ICG to total ICG initially used for encapsulation. All loading measurements were performed in triplicate.

Micelle Formulation and Characterization

Micelles were assessed for size, shape, composition and in vitro stability. Micelles were prepared at one mg/ml at the following ratios of PEO-PHB-PEO to PF-127: 10:0, 7:3, 5:5, 3:7, 0:10. The effective diameter of the micelles was measured using a ZetaPlus dynamic light scattering (DLS) instrument (Brookhaven Instrument Co., Holtsville, N.Y.) at a wavelength of 659 nm with a 90 degree detection angle at both 25° C. and 37° C. Each sample was analyzed in triplicate and the effective diameter of the micelle formulation was reported. Results are shown in FIG. 1. Particle sizing of the ICG-loaded micelles exhibited temperature-dependent behavior in the micelle architectures. At room temperature, PEO-PHB-PEO only and mixed micelles had average effective diameters between about 100 and 110 nm. No room temperature data is available for pure PF-127 micelles, because stable micelles are not formed by the evaluated concentration PF-127 at room temperature. At 37° C., however, a thermosensitive transition was induced in the mixed micelle formulations. The mean effective micelle diameter was 118 nm for the 10:0 formulation; 110 nm for the 7:3 formulation, 99 nm for the 5:5 formulation, 81 nm for the 3:7 formulation, and 25.6 nm for the 0:10 formulation.

ICG-loaded PEO-PHB-PEO:PEO-PPO-PEO mixed micelles (7:3 ratio) were photographed using cryo-transmission micrography. Results are shown in FIG. 2. Surprisingly, the micelles assembled into filamentous structures.

To confirm that PF-127 and PEO-PHB-PEO were self-assembling into heterogeneous nanoparticles rather than concurrent but segregated micelle populations, each copolymer was labeled with a fluorophore to probe spatial colocalization by means of fluorescent resonance energy transfer (FRET). PEO-PHB-PEO was labeled with the donor dye (AlexaFluor 491), while PF-127 was labeled with the acceptor (AlexaFluor 555). To label PEO-PHB-PEO, a PEO-PHB-PEO triblock with a terminal fluorenylmethyloxycarbonyl functional group was synthesized by a two-step variation of the previously described triblock synthesis. Briefly, in the first step, PHB-diol and mPEG-COOH were reacted in a 1:1.2 molar ratio with DCC coupling in the presence of DMAP to yield PEO-PHB diblock. After filtration of precipitated dicyclohexylurea, the diblock was precipitated in diethyl ether and was characterized by NMR and GPC analysis. PEO-PHB diblock was then reacted at a 1:1.2 ratio with Fmoc-PHB-COOH with DCC coupling in the presence of DMAP to yield an Fmoc terminated triblock. After filtration of precipitated dicylcohexylurea, the triblock was handled, filtered, and characterized as described above.

To expose the reactive amine of the Fmoc functional group, Fmoc-PEO-PHB-PEO was mixed for 1 hour at 100 mg/mL in 20% piperidine in DMF (v/v). Liberated Fmoc was detected under UV illumination after isolation via thin-layer chromatography and subsequent iodine staining. An Alexa Fluor® 488 succinimidyl ester dye (Molecular Probes) was conjugated to deprotected Fmoc-PEO-PHB-PEO triblock. To label PF-127, a succinimidyl ester Alexa Fluor® 555 succinimidyl ester dye was conjugated to the terminal amine of Pluronic F127 triblock. Briefly, conjugation was carried out at a 1:1 dye/primary amine ratio in 1× phosphate buffered saline (pH 8.0) at a polymer concentration of 0.5 mg/mL. The reaction solution was mixed for twenty hours and free dye was removed by multiple filtrations through a 3000 kDA MW 3000 molecular weight cutoff centrifuge filter (Pall-Life Sciences).

Close spatial proximity of donor-conjugated PEO-PHB-PEO and acceptor-conjugated PF127 is expected to result in efficient FRET whereas separate populations of PEO-PHB-PEO only and PF127 only micelles would not be concentrated enough to result in energy transfer. A 488/555 FRET dye pairing was employed to verify the proximity of the two triblock types in solution. Energy exchange was measured by mixing 10 mg/mL solutions of each labeled polymer at varying ratios and exciting the FRET pair at 488 and 555 nm, recording emission intensity at 565 nm using a Safire 2 microplate fluorimeter (Tecan, Austria).

Results are shown in FIG. 3. Energy transfer from donor PEO-PHB-PEO to acceptor PF-127 was observed in all mixed micelle formulations, thus confirming that the polymers co-localize in mixed micelle structures. When excited at 491 nm, minimal fluorescence emission was detected from the 0:10 (PF-127 only) micelles, indicating that the vast majority of acceptor fluorescence occurred due to resonant energy transfer from excited donor molecules in the molecule's immediate vicinity (30-60 angstroms). In the mixed micelle formulations, acceptor fluorescence at 565 nm was between 4 and 10-fold higher than in the 0:10 formulations, with the ratio of (donor fluorescence)/(acceptor fluorescence) decreasing with higher fractions of PF-127. These observations provide confirmation that heterogeneous mixed micelles were achieved with this mixture of triblock copolymers.

The effect of mixed micelle polymer ratios on micelle stability was assessed by determining the CMC for each formulation using a static light scattering. The CMC can be identified as the point at which the refractive index curve deviates significantly from a baseline of 0; a sharp increase in refractive index is indicative of spontaneous macromolecular assembly. See, e.g., Holland and Rubingh, *MIXED SURFACTANT SYSTEMS—AN OVERVIEW. Acs Symposium Series* 501:2-30 (1992). Results are shown in TABLE 1. The enhancement of stability of the mixed micelles at room temperature by incorporating PEO-PHB-PEO is clearly evident, as micelles with increasing fractional proportions of PEO-PHB-PEO exhibit lower CMC values.

TABLE 1

| Critical micelle concentrations for mixed micelle formulations at 25° C. | |
|---|---|
| PEO-PHB-PEO:PF-127 | CMC (mg/ml) |
| 10:0 | 0.0135 |
| 7:3 | 0.019 |
| 5:5 | 0.027 |
| 3:7 | 0.042 |

Experiment 2

PEO-PHB-PEO/PEO-PPO-PEO Mixed Micelles Enhance the Stability of Indocyanine Green (ICG)

ICG Loading Efficiency and ICG Content

Lyophilized micelles were weighed and dissolved in 1 mL of dimethyl sulfoxide (DMSO), causing complete dissolution of the micelle and release of the encapsulated ICG. Empty micelles dissolved in DMSO were used as a blank for ICG/ICG-loaded micelle samples. The ICG concentration was determined by comparing absorbance at 775 nm to a standard curve of ICG with a squared correlation coefficient of 0.999 in the linear range of 0-12.5 µM in DMSO. ICG content was expressed as the weight ratio between loaded ICG and total weight of ICG-loaded micelle, and loading efficiency as the weight percent of encapsulated ICG to total ICG initially used for encapsulation. All loading measurements were performed in triplicate.

Stability of ICG Micelles In Vitro

ICG has advantageous fluorescence properties for near-infrared imaging (NIR) in vivo but limitations include the molecule's photo, aqueous, and thermal instability as well as rapid binding to blood proteins and subsequent clearance by the liver. See, e.g., Cherrick, *J. Clin. Invest.* 39:592-600 (1959) and Kirchherr, et al., *Mol. Pharmaceut.* 6:480-491 (2009). Aqueous degradation of ICG occurs as a result of double bond saturation in the molecule's conjugated chain, and sequestering the molecule from the solvent radicals that activate this process reduces the rate of its degradation. See, e.g., Kirchherr et al., and Altinoglu and Adair, *Wiley Interdisciplinary Reviews—Nanomedicine and Nanobiotechnology*, 2:61-477 (2010). To test the ability of the mixed micelle systems to stabilize ICG, the fluorescence of encapsulated dye was monitored over time at both room temperature and 37° C.

Stability of ICG in mixed micelles was evaluated by measuring decay of fluorescence emission in solution over a period of approximately ten days. After preparing ICG-encapsulating mixed micelle solutions as described above, samples were dissolved at 10 mg/mL in deionized water and maintained at room temperature or 37° C. in the dark and under slight agitation for the duration of the study. At predetermined intervals, each mixture was sampled and the fluorescence intensity of the sample was evaluated with excitation at 775 nm and emission from 786 to 850 nm.

Results are shown in FIGS. 4A and 4B. All measurements were normalized to the initial fluorescence at t=0. At both room temperature and 37° C., free ICG rapidly degraded to less than 10% of its original fluorescence value within forty-eight hours. All mixed micelles formulations exhibited improved ICG stability as compared to PEO-PHB-PEO only or PF-127 only micelles. All mixed micelle formulations tested maintained close to 100% of original fluorescence after ten days at room temperature and, after 10 days at 37° C., maintained more than 60% of original fluorescence. ICG in PEO-PHB-PEO (10:0) micelles lost more fluorescence when incubated at 37° C. as compared to incubation at room temperature. The decline in ICG fluorescence in PEO-PHB-PEO micelles at 37° C. decreased as PF-127 was added to make a mixed micelle formulation.

The ability of the mixed micelles to segregate ICG from the aqueous environment significantly reduces the rate of ICG degradation and thus stabilizes the ICG fluorescence. As shown in FIG. 4A, at room temperature each of the micelle formulations significantly reduced the decay of fluorescence intensity compared to free (unencapsulated) ICG. The mixed micelle formulations provided protection, and even enhanced the fluorescence levels of the dye. As shown in FIG. 4B, the mixed micelle system also offers the ability to optimize particle formulation for optimal stabilization of ICG fluorescence at physiological temperature. The optimization is an improvement over previous methods to stabilize ICG. See, e.g., Rodriguez, et al., *J. of Biomed. Optics* 13:014025 (2008) and Saxena, et al., *J. of Photochem. Photobio. B-Biology*, 74:29-38 (2004). FIG. 4B also shows that at physiological temperature, the advantages of incorporation of the thermosensitive PF-127 copolymer are pronounced, and the 3:7 formulation offered the best stabilization of ICG fluorescence over the time period studied. Moreover, this mixed formulation was superior to PF-127 alone despite the fact that the experiment was conducted above PF-127's critical micellization temperature, which suggests intrinsically higher particle stability mirrored in the decreased CMC induced by the PEO-PHB-PEO component.

Stability of ICG Micelles In Vivo and Use as an Imaging Agent

Micelles containing ICG were administered to tumor-bearing mice and the bioavailability of the ICG was assessed. Free ICG or ICG-micelles were administered to mice by tail vein injection in two injections of 10 mg ICG per dose per mouse with thirty minutes between the two injections. It had been shown that double micelle injection resulted in higher plasma ICG concentrations, perhaps due to saturation of phagocytic cells after the first injection. See, e.g., Kim, et al., *Pharma. Res.* 27:1900-1913 (2010). Blood samples were taken at various time points to compare the relative bioavailability of injected ICG formulations. Results are shown in FIG. 5. The PEO-PHB-PEO:PF-127 7:3 ICG micelle formulation exhibited the highest plasma ICG concentration after both the first and second injections. Area under the curve (AUC) for this formulation was 2.5-fold higher than the 10:0 formulation. Interestingly, the AUC for PEO-PHB-PEO:PF127 3:7 micelle formulation was also higher as compared to the PEO-PHB-PEO only micelles. The AUC of the 5:5 micelle formulation was not notably different than that of the PEO-PHB-PEO only micelles.

Full Body/Tissue Fluorescence Imaging Using ICG-Loaded Mixed Micelles

Micelles containing ICG were administered to tumor-bearing mice and the ability of ICG to localize to the tumor was assessed. Tumor-bearing nude mice were used to assess the ability of ICG micelles to localize to a tumor. The tumors were generated from a transformed human cell line. MDA-MB-435 human melanoma cells were cultured in improved MEM (Mediatech Inc., Manassas, Va.) with 10% FBS and 1% antibiotic/antimicrobial at 37° C. in 5% $CO_2$. Pathogen free Balb/c mice were housed in separate cages with normal access to food and water and kept on a twelve hour light-dark cycle. All experimental procedures were performed in accordance with the protocols approved by the Institutional Animal Care and Use Committee at the University of Washington. To generate tumors, the backs of six-week-old male Balb/c mice were shaved and 100 µt of single cell suspension containing $2 \times 10^6$ MDA-MB-435 cells in serum-free IMEM were injected subcutaneously under anesthesia.

To determine efficiency of ICG accumulation in tumors, whole-body MR fluorescence images of ICG were collected two and twenty-four hours after administration of ICG to MDA-MB-435 tumor-bearing mice. ICG and ICG-loaded micelle solutions (150 µt) were injected intravenously (i.v.) through the tail vein of the MDA-435 tumor-bearing mice at a dose of 10 µg ICG. A second injection was performed with the same dose of ICG and ICG-loaded micelles thirty minutes following the initial injection. Blood was collected at various time points, and all the mice were sacrificed at the last time point to collect the liver, lung, heart, kidney, spleen, and tumor. A fluorescence-based assay was used to analyze ICG in the biological samples. See, e.g., Yin and Bae, *Eur. J. Pharma. Biopharma.* 71:223-230. (2009). Briefly, the blood samples were diluted by adding 100 µL of DMSO, and ICG was extracted for ten minutes. Tissue samples were homogenized with 1 mL of DMSO, followed by overnight extraction at room temperature in the dark. The mixtures of blood and tissues were then centrifuged at 10,000 rpm for ten minutes and the supernatant containing the extracted ICG was measured by fluorescence spectroscopy. The fluorescence intensity of ICG in plasma was normalized by protein content as measured by BCA Protein Assay Kit (Pierce, Rockford, Ill.). The amount of ICG in tissue was calculated according to a standard curve with a squared correlation coefficient of 0.993 in the linear range of 0-0.25 µg/mL and normalized by weight of tissue. The tissue and plasma samples from the non-treated animals were analyzed to determine the background fluorescence.

To evaluate biodistribution of ICG in the murine tumor model, animals were imaged noninvasively at two and twenty-four hours to determine whether ICG was accumulating in the subcutaneous xenografts on the animals' right flanks. Results are shown in FIG. 6. Two hours after injection, the fluorescence image was dominated by signal from the liver and injection site. However, twenty-four hours after injection, ICG was eliminated from most of the body and tumor-specific ICG accumulation was evident. A comparison of tumor accumulation of the various ICG formulations revealed a trend similar to that observed in the blood circulation data; the polymer ratio of 7:3 resulted in maximal ICG fluorescence in the vicinity of the tumor (right flank). Moreover, the 5:5 formulation provided little stabilization of fluorescence intensity when compared to the other polymer ratios.

After whole body imaging at twenty-four hours, tumor tissues were collected and analyzed for fluorescence intensity and size comparison. Tumor size was not uncharacteristically dispersed across the groups. (Data not shown.) To calculate the average radiant efficiency of each tumor, region of interest (ROI) analysis was conducted on the tumor tissues. As shown in FIG. 7, mice treated with the 7:3 mixed micelle formulation showed a statistically significant increase in ICG fluorescence signal in the tumor tissue when compared to mice treated with the 10:0 formulation or free ICG. This improvement mirrored the enhanced bioavailability of this 7:3 formulation.

Experiment 3

Administration of Doxorubicin Using PEO-PHB-PEO/PEO-PPO-PEO Mixed Micelles

Mixtures of the amphiphilic triblock copolymers PEO-PHB-PEO and PF-127 were used to formulate mixed micelles. Doxorubicin, an anthracycline antibiotic used to mitigate solid tumor growth was loaded into the micelles via chloroform emulsification.

The cell lines which were used were the MDA-MB-435 (Parent) and MDA-MB-435-MDR (MDR) cell lines. The MDR cell line exhibits resistance to treatment by doxorubicin via the presence of cell efflux pumps which exclude doxorubicin from the cytosol of the cells.

Loading Content

Doxorubicin was loaded into mixed micelles via emulsification in chloroform. Unencapsulated doxorubicin was removed via high speed centrifugation. Loading content (micrograms of doxorubicin per milligram of polymer), was determined by absorbance of doxorubicin (480 nm) and normalized to polymer mass. Results are shown in FIG. 8. Loading content is related to polymer ratio, and increases as the ratio of PHB triblock is increased.

Cytotoxicity

Cytotoxicity was measured by treating MDA-MB-435 (Parent) and MDA-MB-435-MDR cells for 4 hours with free doxorubicin and encapsulated doxorubicin using various formulations of mixed micelles. After 4 hours the doxorubicin was rinsed from the cells. After 24 hours the cell viability was measured using an MTS assay. MDA-MB-435 cells were treated with 4 µg/mL DOX, and MDA-MB-435 cells were treated with 16 µg/mL DOX.

Results are shown in FIGS. 9A and 9B. Unencapsulated DOX had limited effect in drug resistant (MDR) cells, as expected. Encapsulating DOX in micelles increased cytotoxicity in an MDR cell line.

Tumor Reduction

Tumor reduction was measured in both the MDA-MB-435 (Parent) and MDA-MB-435-MDR (MDR) cell lines. Dual xenografts were established via injection of two million cells subcutaneously on the left and right rear flank of nude mice. Parent cells were injected on the left, and MDR cells were injected on the right. Tumors were allowed to develop for 2.5 weeks.

Encapsulated doxorubicin and free doxorubicin was administered in three doses at 6 mg/kg (separated by 3 days). The following treatment groups were included in the study:

| 1) | 10:0 | PHB triblock:PF-127 | (Encapsulated DOX) |
| 2) | 7:3 | " | (Encapsulated DOX) |
| 3) | 3:7 | " | (Encapsulated DOX) |
| 4) | | Free DOX | |
| 5) | | Control (No treatment) | |

Long and short tumor axis lengths were measured every 4 days for a total of 37 days after the first injection and tumor volume was calculated using the following relationship:

$$\text{Tumor volume} = \frac{(\text{Long axis})(\text{Short axis})^2}{2}$$

Results are shown in FIGS. 10A and 10B. Tumor growth was suppressed in both cell lines. MDR tumor suppression was comparable to that of unencapsulated DOX.

Weight loss was measured concurrently with tumor measurements, as shown in FIG. 11. Encapsulating DOX within micelles minimized toxicity associated weight loss.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A method of delivering an imaging agent to a subject, the method comprising the step administering a mixed micelle comprising the imaging agent to the subject, wherein the mixed micelle comprises (a) a poly(ethylene oxide)-poly[(R)-3-hydroxybutyrate]-poly(ethylene oxide) (PEO-PHB-PEO) molecule synthesized from poly[(R)-3-hydroxybutyrate] diol with a molecular weight of about 2,300 Da and methoxy-poly(ethylene glycol) monocarboxylic acid having a molecular weight of about 4,900 Da and (b) a poly(ethylene oxide)-poly(propylene oxide)-poly(ethylene oxide) (PEO-PPO-PEO) molecule having a molecular weight of about 12,600 wherein each PEO polymer block has about 100 PEO repeat units and the PPO polymer block has about 65 PPO repeat units, wherein the ratio of PEO-PHB-PEO to PEO-PPO-PEO is between about 7.7:3.3 and 6.3:2.7.

2. The method of claim 1, wherein the imaging agent is a member selected from the group consisting of indocyanine green (ICG), gadolinium or manganese, iron oxide nanoparticles, quantum dots, iodine and barium.

3. The method of claim 2, wherein the imaging agent is indocyanine green (ICG).

4. The method of claim 1, wherein the imaging agent is more stable in the subject when administered in the mixed micelle, than when administered in an aqueous solution.

5. The method of claim 1, wherein the subject has a tumor and the mixed micelle comprising the imaging agent is preferentially taken up by the tumor.

6. The method of claim 1, further comprising a step of visualizing the imaging agent in the subject.

7. The method of claim 1, wherein the size of the mixed micelle is between 10-120 nm.

8. The method of claim 1, wherein the size of the mixed micelle is between 50-120 nm.

9. The method of claim 1, wherein the size of the mixed micelle is about 110 nm.

10. The method of claim 1, wherein the mixed micelle is a filamentous micelle.

11. The method of claim 1, further comprising the step of adding the mixed micelle to a pharmaceutical carrier.

* * * * *

UNITED STATES PATENT AND TRADEMARK OFFICE
CERTIFICATE OF CORRECTION

PATENT NO. : 9,655,981 B2
APPLICATION NO. : 15/048098
DATED : May 23, 2017
INVENTOR(S) : Wayne R. Gombotz et al.

It is certified that error appears in the above-identified patent and that said Letters Patent is hereby corrected as shown below:

In the Specification

| Column | Line | ERROR |
| --- | --- | --- |
| 15 | 64 | "e.g., MR." should read --e.g., NIR.-- |
| 17 | 12 | "(MB)" should read --(PHB)-- |
| 21 | 34 | "10 mg" should read --10 µg-- |
| 21 | 67 | "100 µt" should read --100 µL-- |
| 22 | 4 | "whole-body MR" should read --whole-body NIR-- |
| 22 | 7 | "(150 µt)" should read --(150 µL)-- |

Signed and Sealed this
Nineteenth Day of December, 2017

Joseph Matal
*Performing the Functions and Duties of the
Under Secretary of Commerce for Intellectual Property and
Director of the United States Patent and Trademark Office*